US009236635B2

(12) United States Patent
Abe et al.

(10) Patent No.: US 9,236,635 B2
(45) Date of Patent: Jan. 12, 2016

(54) NON-AQUEOUS ELECTROLYTE AND ELECTRICITY STORAGE DEVICE USING SAME

(75) Inventors: Koji Abe, Yamaguchi (JP); Kei Shimamoto, Yamaguchi (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 80 days.

(21) Appl. No.: 14/237,492

(22) PCT Filed: Aug. 7, 2012

(86) PCT No.: PCT/JP2012/070098
§ 371 (c)(1),
(2), (4) Date: Feb. 6, 2014

(87) PCT Pub. No.: WO2013/024748
PCT Pub. Date: Feb. 21, 2013

(65) Prior Publication Data
US 2014/0154587 A1 Jun. 5, 2014

(30) Foreign Application Priority Data

Aug. 12, 2011 (JP) .................................. 2011-176589
Oct. 14, 2011 (JP) .................................. 2011-227414

(51) Int. Cl.
| | |
|---|---|
| *H01M 10/0567* | (2010.01) |
| *H01M 10/0569* | (2010.01) |
| *H01M 10/0525* | (2010.01) |
| *H01M 4/131* | (2010.01) |
| *H01M 4/505* | (2010.01) |
| *H01M 4/52* | (2010.01) |
| *H01M 4/58* | (2010.01) |
| *H01M 4/583* | (2010.01) |
| *H01M 4/38* | (2006.01) |
| *H01M 4/485* | (2010.01) |

(Continued)

(52) U.S. Cl.
CPC ........... *H01M 10/0567* (2013.01); *C07C 69/65* (2013.01); *C07C 309/65* (2013.01); *C07D 327/00* (2013.01); *H01M 4/131* (2013.01); *H01M 4/386* (2013.01); *H01M 4/387* (2013.01); *H01M 4/485* (2013.01); *H01M 4/505* (2013.01); *H01M 4/52* (2013.01); *H01M 4/583* (2013.01); *H01M 4/5825* (2013.01); *H01M 10/052* (2013.01); *H01M 10/0525* (2013.01); *H01M 10/0568* (2013.01); *H01M 10/0569* (2013.01); *Y02E 60/122* (2013.01); *Y02T 10/7011* (2013.01)

(58) Field of Classification Search
CPC ..................... H01M 10/0567; H01M 10/0569; H01M 10/0568; H01M 10/0525; H01M 4/131; H01M 4/505; H01M 4/52; H01M 4/5825; H01M 4/583; H01M 4/386; H01M 4/387; H01M 4/485; Y02E 60/122
See application file for complete search history.

(56) References Cited

U.S. PATENT DOCUMENTS

| 2004/0043300 A1 | 3/2004 | Utsugi et al. |
| 2004/0096750 A1 | 5/2004 | Kim et al. |

FOREIGN PATENT DOCUMENTS

| DE | 951 928 | 11/1956 |
| JP | 2002 367673 | 12/2002 |
| JP | 2002 367674 | 12/2002 |
| JP | 2004 172120 | 6/2004 |
| JP | 2004 281368 | 10/2004 |
| JP | 2011 071098 | 4/2011 |
| WO | 2005 057714 | 6/2005 |

OTHER PUBLICATIONS

Ringier, B.H, "Ueber stiockstoffhaltige Derivate der Methionsaeure", Helvetica Chimica Acta, pp. 1790-1795, 1944.

(Continued)

*Primary Examiner* — Laura Weiner
(74) *Attorney, Agent, or Firm* — Oblon, McClelland, Maier & Neustadt, L.L.P.

(57) ABSTRACT

The present invention provides a nonaqueous electrolytic solution capable of improving electrochemical characteristics in a broad temperature range, such as low-temperature cycle properties and low-temperature discharge properties after high-temperature storage, and provides an energy storage device using the nonaqueous electrolytic solution. The invention includes (1) a nonaqueous electrolytic solution of an electrolyte salt dissolved in a nonaqueous solvent, which comprises from 0.001 to 10% by mass of a compound represented by the following general formula (I), and (2) an energy storage device comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of (1).

(I)

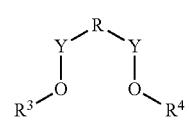

(In the formula, Y represents a group —C(=O)— or a group —S(=O)$_2$—; R$^3$ and R$^4$ each independently represent an aryl group having from 6 to 10 carbon atoms in which at least one hydrogen atom is substituted with a halogen atom, or R$^3$ and R$^4$ bonding to each other represent a cycloalkanediyl group or a benzenediyl group, having from 5 to 12 carbon atoms. R represents —C(R$^1$)(R$^2$)— or -L-; R$^1$ and R$^2$ each independently represent a hydrogen atom, a halogen atom, or an alkyl group having from 1 to 4 carbon atoms; and L represents a divalent linking group having from 1 to 6 carbon atoms and optionally substituted with a halogen atom).

11 Claims, No Drawings

(51) Int. Cl.
*C07C 309/65* (2006.01)
*H01M 10/052* (2010.01)
*C07C 69/65* (2006.01)
*C07D 327/00* (2006.01)
*H01M 10/0568* (2010.01)

(56) References Cited

OTHER PUBLICATIONS

International Search Report Issued Dec. 4, 2012 in PCT/JP12/070098 Filed Aug. 7, 2012.

NON-AQUEOUS ELECTROLYTE AND ELECTRICITY STORAGE DEVICE USING SAME

TECHNICAL FIELD

The present invention relates to a nonaqueous electrolytic solution capable of improving electrochemical characteristics in a broad temperature range, and an energy storage device using it.

BACKGROUND ART

In recent years, energy storage devices, especially lithium secondary batteries have been widely used in small-sized electronic devices, such as mobile telephones, notebook-size personal computers and the like, in electric vehicles, and for electric power storage. These electronic devices and vehicles may be used in a broad temperature range at midsummer high temperatures or at frigid low temperatures, and are therefore required to have well-balanced and improved electrochemical characteristics in a broad temperature range.

In particular, for preventing global warming, $CO_2$ emission reduction has now become imperative, and among environment-responsive vehicles equipped with energy storage devices such as lithium secondary batteries, capacitors and the like, early popularization of hybrid electric vehicles (HEV), plug-in hybrid electric vehicles (PHEV) and battery electric vehicles (BEV) is desired. Vehicles may take a long travel distance and therefore may be used in the region of a widely-varying temperature range that covers from an extremely hot region of the tropical zone to a frigid region. Consequently, it is required that the electrochemical characteristics of those storage devices to be mounted on such vehicles should not be deteriorated even in use in a broad temperature range varying from high temperatures to low temperatures.

In this specification, the term of lithium secondary batteries is used as the concept that includes also so-called lithium ion secondary batteries.

A lithium secondary battery is mainly constituted of a positive electrode and a negative electrode containing a material capable of absorbing and releasing lithium, and a nonaqueous electrolytic solution containing a lithium salt and a nonaqueous solvent. For the nonaqueous solvent, used are carbonates, such as ethylene carbonate (EC), propylene carbonate (PC), etc.

As the negative electrode of the lithium secondary battery, known are metal lithium, and metal compounds (metal elemental substances, oxides, alloys with lithium, etc.) and carbon materials capable of absorbing and releasing lithium. In particular, a lithium secondary battery using a carbon material capable of absorbing and releasing lithium, such as coke, artificial graphite, natural graphite or the like, has been widely put into practical use.

For example, it is known that, in a lithium secondary battery that uses a highly-crystallized carbon material, such as natural graphite, artificial graphite or the like, as the negative electrode material therein, the solvent in the nonaqueous electrolytic solution undergoes reductive decomposition on the surface of the negative electrode during charging and the decomposed products and gases generated through the decomposition detract from the desired electrochemical reaction in the battery to thereby worsen the cycle properties of the battery. In addition, when the decomposed products of the nonaqueous solvent accumulate, then lithium could not be smoothly absorbed and released by the negative electrode and the electrochemical characteristics of the battery would be thereby worsened in a broad temperature range.

Further, it is known that a lithium secondary battery using a lithium metal or its alloy, or a metal elemental substance, such as tin, silicon or the like or its metal oxide as the negative electrode material therein may have a high initial battery capacity but the battery capacity and the battery performance thereof, such as cycle properties greatly worsens, since the micronized powdering of the material is promoted during cycles thereby bringing about accelerated reductive decomposition of the nonaqueous solvent, as compared with the negative electrode of a carbon material. In addition, the micronized powdering of the negative electrode material and the accumulation of the decomposed products of the nonaqueous solvent would interfere with smooth absorption and release of lithium by the negative electrode, thereby often worsening the electrochemical characteristics in a broad temperature range of the battery.

On the other hand, it is also known that, in a lithium secondary battery using, for example, $LiCoO_2$, $LiMn_2O_4$, $LiNiO_2$, $LiFePO_4$ or the like as the positive electrode, the nonaqueous solvent in the nonaqueous electrolytic solution locally undergoes partial oxidative decomposition in the interface between the positive electrode material and the nonaqueous electrolytic solution in a charged state and the decomposed products and gases generated through the decomposition interfere with the desired electrochemical reaction in the battery, thereby also worsening the electrochemical characteristics in a broad temperature range of the battery.

As in the above, the decomposed products and gases generated through decomposition of the nonaqueous electrolytic solution in the positive electrode and the negative electrode interfere with lithium ion movement and cause battery swelling, and the battery performance is thereby worsened. Despite the situation, electronic appliances equipped with lithium secondary batteries therein are offering more and more an increasing range of functions and are being in a stream of further increase in power consumption. With that, the capacity of lithium secondary batteries is being much increased, and the space volume for the nonaqueous electrolytic solution in the battery is decreased by increasing the density of the electrode and by reducing the useless space volume in the battery. Accordingly, the situation is that even decomposition of only a small amount of nonaqueous electrolytic solution may worsen the electrochemical characteristics in a broad temperature range of the battery.

PTL 1 proposes a nonaqueous electrolytic solution containing 1,5,2,4-dioxadithiepane 2,2,4,4-tetraoxide, and suggests improvement of cycle properties and storage properties.

PTL 2 proposes a nonaqueous electrolytic solution containing diphenylmethane disulfonate, and suggests improvement of cycle properties and storage properties.

PTL 3 proposes a nonaqueous electrolytic solution containing dimethyl malonate, and suggests improvement of overcharge properties.

PTL 4 proposes a nonaqueous electrolytic solution containing 2,4-difluorophenyl acetate, and suggests improvement of overcharge properties and storage properties.

CITATION LIST

Patent Literature

PTL 1: JP-A 2004-281368

PTL 2: WO2005/057714

PTL 3: JP-A 2002-367673

PTL 4: JP-A 2011-71098

SUMMARY OF INVENTION

Technical Problem

An object of the present invention is to provide a nonaqueous electrolytic solution capable of improving electrochemical characteristics in abroad temperature range, and an energy storage device using it.

Solution to Problem

The present inventors have investigated in detail the performance of the nonaqueous electrolytic solutions in the above-mentioned prior art. As a result, the current situation is that the nonaqueous electrolytic solutions of the above-mentioned patent literature could not be said to be sufficiently satisfactory for the problem of improving the electrochemical characteristics in abroad temperature range, such as low-temperature cycle properties and low-temperature discharge properties after high-temperature storage of batteries.

Given the situation, the present inventors have assiduously studied for the purpose of solving the above-mentioned problems, and have found that, when at least one specific compound is added to a nonaqueous electrolytic solution of an electrolyte salt dissolved in a nonaqueous solvent, then the electrochemical characteristics, especially those of lithium batteries in a broad temperature range can be improved, and have completed the present invention.

Specifically, the present invention provides the following (1) to (6).

(1) A nonaqueous electrolytic solution of an electrolyte salt dissolved in a nonaqueous solvent, which comprises from 0.001 to 10% by mass of a compound represented by the following general formula (I).

[Chem. 1]

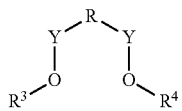

(I)

(In the formula, Y represents a group —C(=O)— or a group —S(=O)$_2$—; $R^3$ and $R^4$ each independently represent an aryl group having from 6 to 10 carbon atoms in which at least one hydrogen atom is substituted with a halogen atom, or $R^3$ and $R^4$ bonding to each other represent a cycloalkanediyl group or a benzenediyl group, having from 5 to 12 carbon atoms. The cycloalkanediyl group and the benzenediyl group may have a substituent.

R represents —C($R^1$)($R^2$)— or -L-; $R^1$ and $R^2$ each independently represent a hydrogen atom, a halogen atom, or an alkyl group having from 1 to 4 carbon atoms; and L represents a divalent linking group having from 1 to 6 carbon atoms and optionally substituted with a halogen atom.)

(2) A nonaqueous electrolytic solution of an electrolyte salt dissolved in a nonaqueous solvent, which comprises from 0.001 to 10% by mass of a compound represented by the following general formula (II).

[Chem. 2]

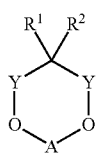

(II)

(In the formula, Y represents a group —C(=O)— or a group —S(=O)$_2$—; $R^1$ and $R^2$ each independently represent a hydrogen atom, a halogen atom, or an alkyl group having from 1 to 4 carbon atoms; and A represents a cycloalkanediyl group or a benzenediyl group, having from 5 to 12 carbon atoms, which may have a substituent.)

(3) A nonaqueous electrolytic solution of an electrolyte salt dissolved in a nonaqueous solvent, which comprises from 0.001 to 10% by mass of a compound represented by the following general formula (III).

[Chem. 3]

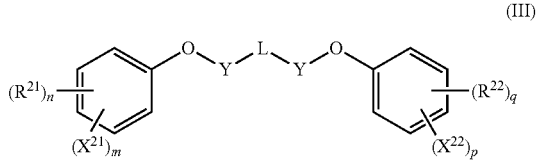

(III)

(In the formula, Y represents a group —C(=OC)— or a group —S(=O)$_2$—; $R^{21}$ and $R^{22}$ each independently represent a halogenoalkyl group having from 1 to 4 carbon atoms; $X^{21}$ and $X^{22}$ each independently represent a halogen atom; L represents a divalent linking group having from 1 to 6 carbon atoms and optionally substituted with a halogen atom. m, n, p and q each indicate an integer of from 0 to 5, satisfying 1≤m+n≤5 and 1≤p+q≤5.)

(4) An energy storage device comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of any of the above (1) to (3).

(5) A cycloalkanedisulfonate compound represented by the following general formula (II-1).

[Chem. 4]

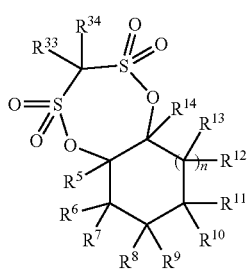

(II-1)

(In the formula, $R^{33}$ and $R^{34}$ each independently represent a hydrogen atom, a halogen atom, or an alkyl group having from 1 to 4 carbon atoms; and $R^5$ to $R^{14}$ each independently represent a hydrogen atom, an alkyl group having from 1 to 6 carbon atoms, an alkenyl group having from 2 to 6 carbon atoms, an alkynyl group having from 2 to 6 carbon atoms, an aryl group having from 6 to 12 carbon atoms, or an alkoxy group having from 1 to 6 carbon atoms, they may bond to each other to form a ring structure, and the hydrogen atom thereof may be substituted with a halogen atom. n indicates an integer of from 0 to 3.)

(6) An alkanedisulfonate compound represented by the following general formula (III-1).

[Chem. 5]

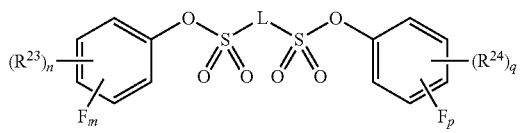

(III-1)

(In the formula, $R^{23}$ and $R^{24}$ each independently represent a fluoroalkyl group having from 1 to 4 carbon atoms; L represents a divalent linking group having from 1 to 6 carbon atoms and optionally substituted with a halogen atom. m, n, p and q each indicate an integer of from 0 to 5, satisfying $1 \leq m+n \leq 5$ and $1 \leq p+q \leq 5$.)

Advantageous Effects of Invention

According to the present invention, there are provided a nonaqueous electrolytic solution capable of improving electrochemical characteristics in a broad temperature range, especially low-temperature cycle properties and low-temperature discharge properties after high-temperature storage, and an energy storage device, such as lithium batteries and others using the nonaqueous electrolytic solution.

DESCRIPTION OF EMBODIMENTS

[Nonaqueous Electrolytic Solution]

The nonaqueous electrolytic solution of the present invention comprises an electrolyte salt dissolved in a nonaqueous solvent, and comprises from 0.001 to 10% by mass of a compound represented by the following general formula (I).

[Chem. 6]

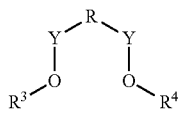

(I)

(In the formula, Y, $R^3$ and $R^4$ are the same as above.)

The present invention includes the following first aspect and second aspect, as preferred embodiments thereof.

The first aspect of the present invention is a nonaqueous electrolytic solution of an electrolyte salt dissolved in a nonaqueous solvent, which comprises from 0.001 to 10% by mass of a compound represented by the following general formula (II).

[Chem. 7]

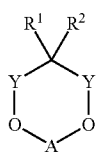

(II)

(In the formula, Y, $R^1$, $R^2$ and A are the same as above.)

The second aspect of the present invention is a nonaqueous electrolytic solution of an electrolyte salt dissolved in a nonaqueous solvent, which comprises from 0.001 to 10% by mass of a compound represented by the following general formula (III).

[Chem. 8]

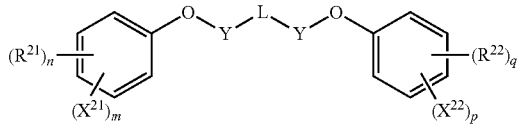

(III)

(In the formula, Y, $R^{21}$, $R^{22}$, $X^{21}$, $X^{22}$, L, m, n, p and q are the same as above.)

Though not always clear, the reason why the nonaqueous electrolytic solution of the present invention, especially that of the first aspect of the present invention can remarkably improve the electrochemical characteristics thereof in a broad temperature range may be considered as follows:

The compound represented by the general formula (II) in the first aspect of the present invention has the functional group Y of a carbonyl group (—C(=O)—) or a sulfonyl group (—S(=O)$_2$—) having high electrophilicity, and has a divalent linking group of a cycloalkanediyl group having from 5 to 12 carbon atoms or a benzenediyl group, that is highly bulky and has high hydrophobicity. The functional group Y contributes toward forming a dense and highly heat-resistant surface film on a negative electrode, but the highly-bulky divalent linking group can prevent the surface film from being excessively densified, and in addition, the highly-hydrophobic linking group improves the wettability of the compound for separator. As a result, it is considered that the compound could markedly improve the low-temperature cycle properties and the low-temperature discharge properties after high-temperature storage of batteries, which, however, could not be attained by any other compound having the functional group Y but not having a bulky and highly-hydrophobic divalent linking group, for example, 1,5,2,4-dioxadithiepane 2,2,4,4-tetraoxide.

Though also not always clear, the reason why the nonaqueous electrolytic solution of the present invention, especially that of the second aspect of the present invention can remarkably improve the electrochemical characteristics thereof in a broad temperature range may be considered as follows:

The compound represented by the general formula (III) in the second aspect of the present invention has a halogen atom-having phenoxy group, the functional group Y of a carbonyl group (—C(=O)—) or a sulfonyl group (—S(=O)$_2$—) having high electrophilicity, and the divalent linking group L. The functional group Y and the halogen atom-having phenoxy group contribute toward forming a dense and highly heat-resistant surface film on a negative electrode, but the divalent linking group can prevent the surface film from being excessively densified. As a result, it is considered that the compound could markedly improve the low-temperature discharge properties after high-temperature storage of batteries, which, however, could not be attained by any other compound having a halogen atom-having phenoxy group but not having a divalent linking group, for example, 4-fluorophenyl acetate, or any other compound which has a divalent linking chain but in which the phenoxy group does not have a halogen atom, for example, diphenylmethane disulfonate.

The compound contained in the nonaqueous electrolytic solution of the first aspect of the present invention is represented by the following general formula (II).

[Chem. 9]

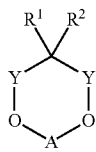

(II)

(In the formula, Y represents a group —C(=O)— or a group —S(=O)$_2$—; R$^1$ and R$^2$ each independently represent a hydrogen atom, a halogen atom, or an alkyl group having from 1 to 4 carbon atoms; and A represents a cycloalkanediyl group having from 5 to 12 carbon atoms or a benzenediyl group, which may have a substituent.)

Preferred examples of the compound represented by the above-mentioned general formula (II) are represented by the general formula (II-2) or the general formula (II-3).

[Chem. 10]

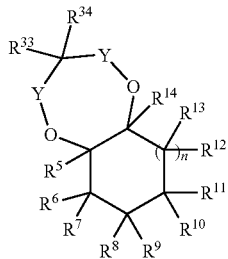

(II-2)

(In the formula, Y is the same as above; R$^{33}$ and R$^{34}$ each independently represent a hydrogen atom, a halogen atom, or an alkyl group having from 1 to 4 carbon atoms; R$^5$ to R$^{14}$ each independently represent a hydrogen atom, an alkyl group having from 1 to 6 carbon atoms, an alkenyl group having from 2 to 6 carbon atoms, an alkynyl group having from 2 to 6 carbon atoms, an aryl group having from 6 to 12 carbon atoms, or an alkoxy group having from 1 to 6 carbon atoms, they may bond to each other to form a ring structure, and the hydrogen atom thereof may be substituted with a halogen atom. n indicates an integer of from 0 to 3.)

[Chem. 11]

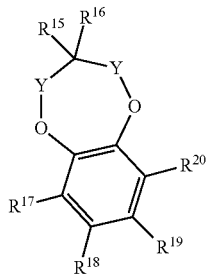

(II-3)

(In the formula, Y is the same as above; R$^{15}$ and R$^{16}$ each independently represent a hydrogen atom, a halogen atom, or an alkyl group having from 1 to 4 carbon atoms; R$^{17}$ to R$^{20}$ each independently represent a hydrogen atom, an alkyl group having from 1 to 6 carbon atoms, an alkenyl group having from 2 to 6 carbon atoms, an alkynyl group having from 2 to 6 carbon atoms, an aryl group having from 6 to 12 carbon atoms, or an alkoxy group having from 1 to 6 carbon atoms, they may bond to each other to form a ring structure, and the hydrogen atom thereof may be substituted with a halogen atom.)

Y in the general formulae (II), (II-2) and (II-3) is more preferably a group —S(=O)$_2$—.

In the general formula (II), the cycloalkanediyl group having from 5 to 12 carbon atoms or the benzenediyl group, that may have a substituent for A includes a 1,2-cyclopentylene group, a 1,2-cyclohexylene group, a 1,2-cycloheptylene group, a 1,2-cyclooctylene group, a 4-propyl-1,2-cyclohexylene group, a 3-vinyl-1,2-cyclohexylene group, a 4-vinyl-1,2-cyclohexylene group, a 4-(1-methylethenyl)-1,2-cyclohexylene group, a 3-(1-methylethyl)-1,2-cyclohexylene group, a 4-(1-methylethyl)-1,2-cyclohexylene group, a 3-methyl-6-(1-methylethyl)-1,2-cyclohexylene group, a 3-methoxy-1,2-cyclohexylene group, a 3-methoxy-3-methyl-6-(1-methylethyl)-1,2-cyclohexylene group, a 1,2-phenylene group, a 3-methyl-1,2-phenylene group, a 3-ethyl-1,2-phenylene group, a 3-propyl-1,2-phenylene group, a 3-chloro-1,2-phenylene group, a 3-fluoro-1,2-phenylene group, a 4-methyl-1,2-phenylene group, a 3,6-dimethyl-1,2-phenylene group, a 3,4,5,6-tetramethyl-1,2-phenylene group, a 3-fluoro-1,2-phenylene group, a 4-fluoro-1,2-phenylene group, a 4-trifluoromethyl-1,2-phenylene group, a 3,6-difluoro-1,2-phenylene group, a 3,4,5,6-tetrafluoro-1,2-phenylene group, etc. Of those, preferred are a 1,2-cyclopentylene group, a 1,2-cyclohexylene group, a 3-vinyl-1,2-cyclohexylene group, a 4-vinyl-1,2-cyclohexylene group, a 1,2-phenylene group, a 3-fluoro-1,2-phenylene group, a 4-fluoro-1,2-phenylene group, and a 4-trifluoromethyl-1,2-phenylene group; and more preferred are a 1,2-cyclohexylene group, a 4-vinyl-1,2-cyclohexylene group, a 1,2-phenylene group, and a 4-fluoro-1,2-phenylene group.

Specific examples of R$^1$, R$^2$, R$^{33}$, R$^{34}$, R$^{15}$ and R$^{16}$ in the above-mentioned general formulae (II), (II-2) and (II-3) include a hydrogen atom, a fluorine atom, a chlorine atom, a bromine atom, a methyl group, an ethyl group, an n-propyl group, an n-butyl group, an n-pentyl group, an n-hexyl group, an iso-propyl group, a sec-butyl group, a tert-butyl group, a trifluoromethyl group, a 2,2,2-trifluoroethyl group, etc. Of those, preferred are a hydrogen atom, a fluorine atom, methyl group and an ethyl group; and more preferred is a hydrogen atom.

Specific examples of R$^5$ to R$^{14}$ in the general formula (II-2) include a hydrogen atom, an alkyl group, such as a methyl group, an ethyl group, an n-propyl group, an n-butyl group, an n-pentyl group, an n-hexyl group, an iso-propyl group, a sec-butyl group, a tert-butyl group, etc.; an alkenyl group, such as an ethenyl group, a 2-propenyl group, a 2-butenyl group, a 3-butenyl group, a 4-pentenyl group, a 5-hexenyl group, a 2-methyl-2-propenyl group, a 3-methyl-2-butenyl group, etc.; an alkynyl group, such as a 2-propynyl group, a 3-butynyl group, a 4-pentynyl group, a 5-hexynyl group, a 2-methyl-2-propynyl group, a 2,2-dimethyl-2-propynyl group, etc.; an aryl group such as a phenyl group, a 2-methylphenyl group, a 3-methylphenyl group, a 4-methylphenyl group, a 4-tert-butylphenyl group, a 2,4,6-trimethylphenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 2,4,6-trifluorophenyl group, a pentafluorophenyl group, a 4-trifluoromethylphenyl group, etc. Of those, preferably, R$^5$ to R$^{14}$ each independently represent a hydrogen atom, an alkyl group having from 1 to 4 carbon atoms, an alkenyl group having from 2 to 4 carbon atoms, or an alkynyl group having from 2 to 4 carbon atoms, more preferably a hydrogen atom, an alkyl group having 1 or 2 carbon atoms, or an alkenyl group having from 2 to 4 carbon atoms, even more preferably a hydrogen atom, a methyl group, an ethyl group, an ethenyl group or a 2-propenyl group, still more preferably a hydrogen atom, a methyl group or an ethenyl group.

Specific examples of $R^{17}$ to $R^{20}$ in the general formula (II-3) include a hydrogen atom, a fluorine atom, a chlorine atom, a bromine atom, a methyl group, an ethyl group, an n-propyl group, an n-butyl group, an n-pentyl group, an n-hexyl group, an isopropyl group, a sec-butyl group, a tert-butyl group, a trifluoromethyl group, a 2,2,2-trifluoroethyl group, etc. Of those, preferred are a hydrogen atom, a halogen atom, and an alkyl group with from 1 to 4 carbon atoms in which at least one hydrogen atom may be substituted with a halogen atom; more preferred are a hydrogen atom, a fluorine atom, a methyl group, an ethyl group and a trifluoromethyl group; and even more preferred are a hydrogen atom, a fluorine atom and a trifluoromethyl group.

As the compounds represented by the general formula (II), concretely mentioned are the following compounds.

[Chem. 12]

A-1
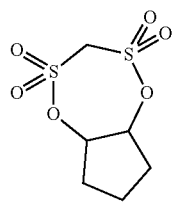

A-2
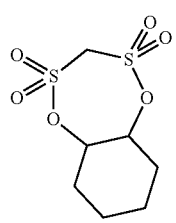

A-3
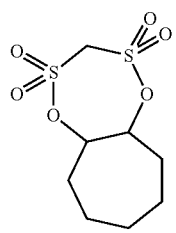

A-4
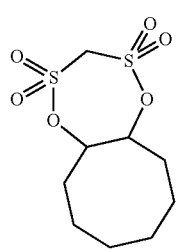

A-5
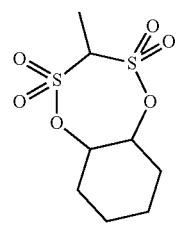

A-6
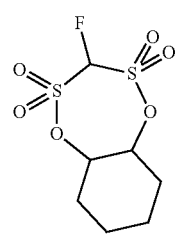

A-7
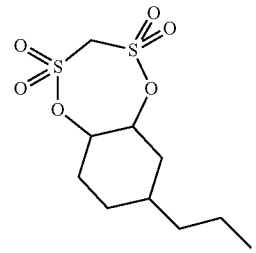

A-8
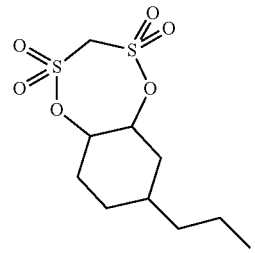

A-9
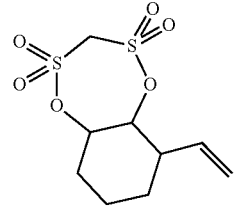

A-10
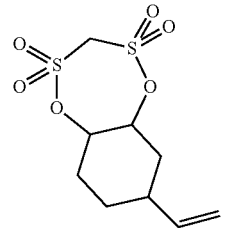

A-11 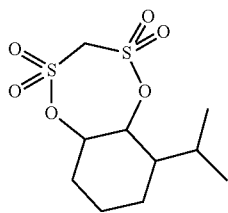
A-12 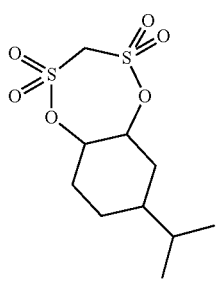
A-13 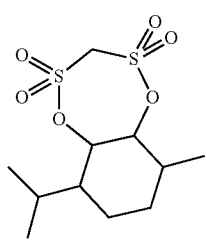
A-14 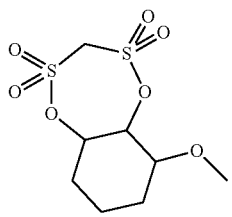
A-15 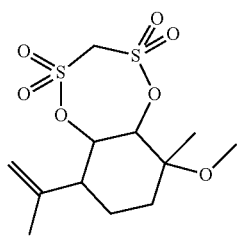
[Chem. 13]
A-16 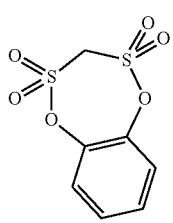
A-17 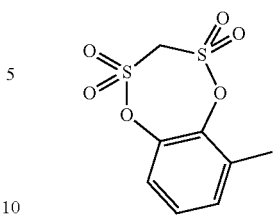
A-18 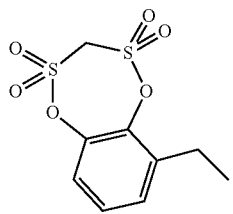
A-19 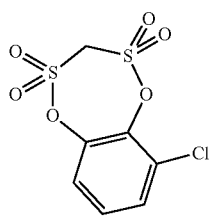
A-20 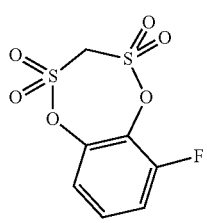
A-21 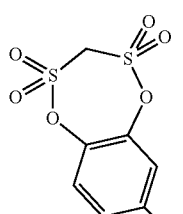
A-22 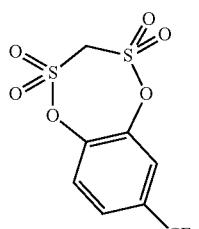
A-23

A-24 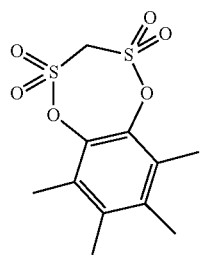
A-25 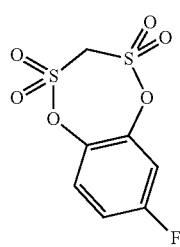
A-26 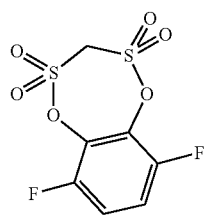
A-27 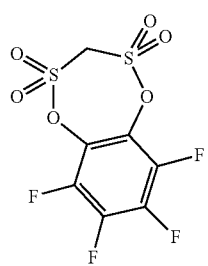
[Chem. 14]
A-28 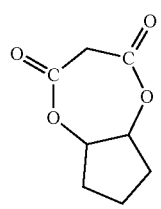
A-29 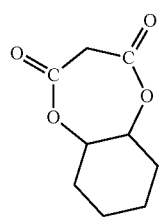
A-30 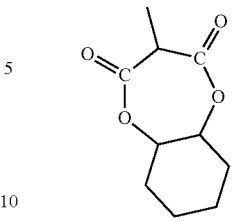
A-31 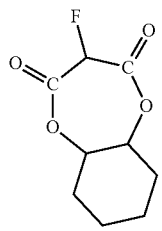
A-32 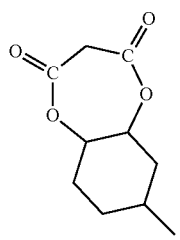
A-33 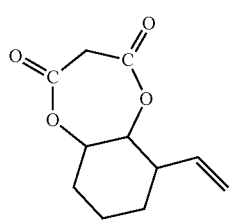
A-34 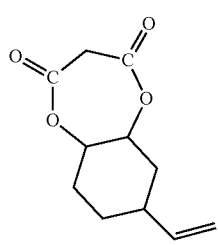
A-35 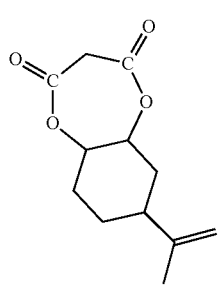

-continued

A-36 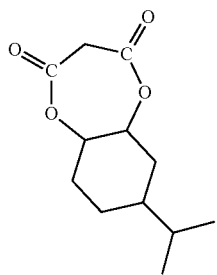

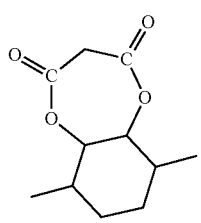

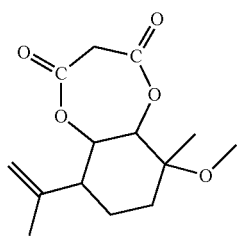

[Chem. 15]

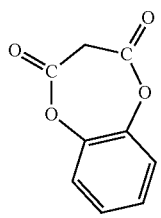

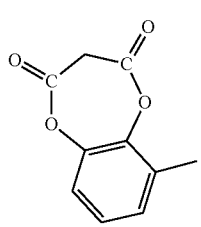

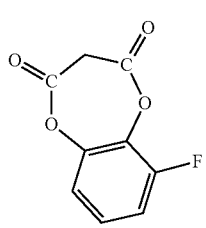

-continued

A-36

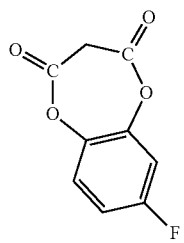 A-42

A-37

A-38 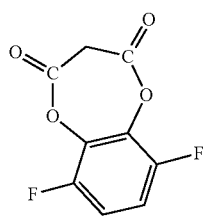 A-43

A-39

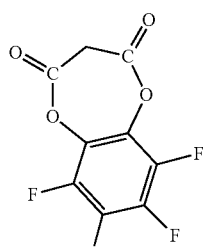 A-44

A-40

A-41

Of the compounds represented by the general formula (II), preferred are one or more selected from the compounds having any of the above-mentioned structures A-1, A-2, A-5, A-6, A-8, A-9, A-16, A-20, A-22, A-25, A-28 to A-30, A-33, A-34, A-39, A-41 and A-42; and more preferred are one or more selected from tetrahydro-5aH-cyclopenta[f][1,5,2,4]dioxadithiepine 2,2,4,4-tetraoxide (structural formula A-1), hexahydrobenzo[f][1,5,2,4]dioxadithiepine 2,2,4,4-tetraoxide (structural formula A-2), 6-vinylhexahydrobenzo[f][1,5,2,4]dioxadithiepine 2,2,4,4-tetraoxide (structural formula A-8), 7-vinylhexahydrobenzo[f][1,5,2,4]dioxadithiepine 2,2,4,4-tetraoxide (structural formula A-9), benzo[f][1,5,2,4]dioxadithiepine 2,2,4,4-tetraoxide (structural formula A-16), 6-fluorobenzo[f][1,5,2,4]dioxadithiepine 2,2,4,4-tetraoxide (structural formula A-20), 7-trifluoromethylbenzo[f][1,5,2,4]dioxadithiepine 2,2,4,4-tetraoxide (structural formula A-22), and 7-fluorobenzo[f][1,5,2,4]dioxadithiepine 2,2,4,4-tetraoxide (structural formula A-25).

The nonaqueous electrolytic solution of the first aspect of the present invention contains, as the compound represented by the general formula (II), one or more selected from the above-mentioned specific examples or preferred examples in an amount of from 0.001 to 10% by mass. When the content is at most 10% by mass, then the risk of excessive formation of a surface film on the electrode to worsen low-temperature properties could be low; and when at least 0.001% by mass, then the surface film formation would be sufficient and the effect of improving high-temperature storage properties could be improved. The content is more preferably at least 0.05% by mass of the nonaqueous electrolytic solution, even more preferably at least 0.2% by mass, and its upper limit is preferably at most 8% by mass, more preferably at most 5% by mass, even more preferably at most 2% by mass.

In the nonaqueous electrolytic solution of the first aspect of the present invention, combining the compound represented by the above-mentioned general formula (II) with the nonaqueous solvent, electrolyte salt and other additives to be mentioned below exhibits a specific effect of synergistically improving electrochemical characteristics in a broad temperature range.

The compound to be contained in the nonaqueous electrolytic solution of the second aspect of the present invention is represented by the following general formula (III).

[Chem. 16]

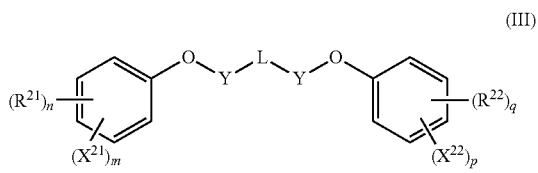

(In the formula, Y represents a group —C(=O)— or a group —S(=O)$_2$—; R$^{21}$ and R$^{22}$ each independently represent a halogenoalkyl group having from 1 to 4 carbon atoms; X$^{21}$ and X$^{22}$ each independently represent a halogen atom; L represents a divalent linking group having from 1 to 6 carbon atoms and optionally substituted with a halogen atom. m, n, p and q each indicate an integer of from 0 to 5, satisfying 1≤m+n≤5 and 1≤p+q≤5.)

Y in the general formula (III) is more preferably a group —S(=O)$_2$—.

In the general formula (III), the divalent linking group having from 1 to 6 carbon atoms and optionally substituted with a halogen atom for L is preferably an alkylene group, such as a methylene group, an ethane-1,2-diyl group, an ethane-1,1-diyl group, a propane-1,3-diyl group, a propane-1,2-diyl group, a propane-1,1-diyl group, a butane-1,4-diyl group, a butane-1,3-diyl group, a 2-methylpropane-1,2-diyl group, a butane-1,1-diyl group, a pentane-1,5-diyl group, a hexane-1,6-diyl group, etc.; or a halogenoalkylene group, such as a monofluoromethylene group, difluoromethylene group, 2-trifluoromethylene group, etc. Of those, preferred is a methylene group, an ethane-1,2-diyl group, an ethane-1,1-diyl group, a propane-1,3-diyl group, a monofluoromethylene group or difluoromethylene group; and more preferred is a methylene group or an ethane-1,2-diyl group.

Preferably, X$^{21}$ and X$^{22}$ in the general formula (III) each are a fluorine atom or a chlorine atom, and more preferably a fluorine atom.

R$^{21}$ and R$^{22}$ in the general formula (III) each represents a halogenoalkyl group having from 1 to 4 carbon atoms in which at least one hydrogen atom is substituted with a halogen atom, and specific examples thereof include a fluoroalkyl group, such as a fluoromethyl group, a difluoromethyl group, a trifluoromethyl group, a 2,2,2-trifluoroethyl group, a perfluoroethyl group, a perfluoropropyl group, a perfluorobutyl group, etc.; a chloroalkyl group, such as a chloromethyl group, a trichloromethyl group, a 2,2,2-trichloroethyl group, etc.; and a bromoalkyl group, such as a bromomethyl group, a 2-bromoethyl group, etc. Of those, preferred is a halogenoalkyl group having 1 or 2 carbon atoms, such as a difluoromethyl group, a trifluoromethyl group, a 2,2,2-trifluoroethyl group, a perfluoroethyl group, a chloromethyl group, a trichloromethyl group, a 2,2,2-trichloroethyl group, etc.; and more preferred is a fluoroalkyl group having 1 or 2 carbon atoms, such as a difluoromethyl group, a trifluoromethyl group, a 2,2,2-trifluoroethyl group, a perfluoroethyl group, etc.

In the general formula (III), m and p each are preferably from 2 to 5, more preferably from 2 to 3. Also preferably, n and q each are from 1 to 3, more preferably from 1 to 2.

The effect of improving electrochemical characteristics in a broad temperature range depends on the position of X$^{21}$, X$^{22}$, R$^{21}$ and R$^{22}$. Preferably, the compound has any of X$^{21}$, X$^{22}$, R$^{21}$ and R$^{22}$ at the ortho- and para-positions thereof, and more preferably has any of X$^{21}$, X$^{22}$, R$^{21}$ and R$^{22}$ in the ortho-position thereof.

As the compounds represented by the general formula (III), concretely mentioned are the following compounds.

(i) When Y is a group C=O, the following compounds are preferred.

[Chem. 17]

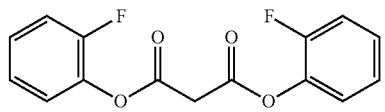

B-1

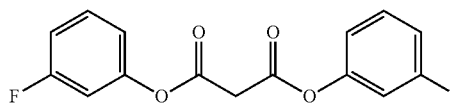

B-2

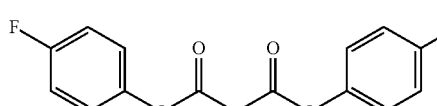

B-3

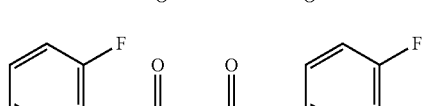

B-4

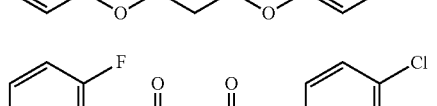

B-5

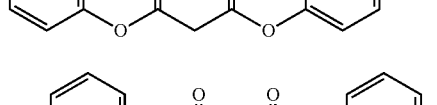

B-6

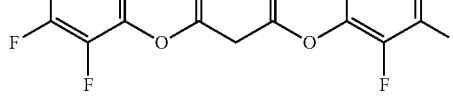

B-7

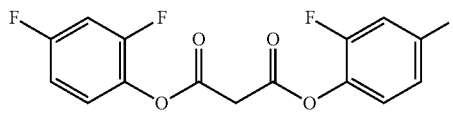

B-8

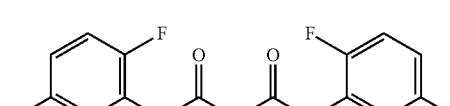

B-9

-continued
B-10
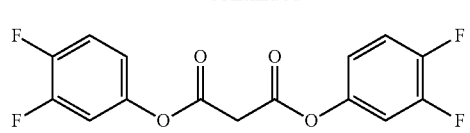
B-11
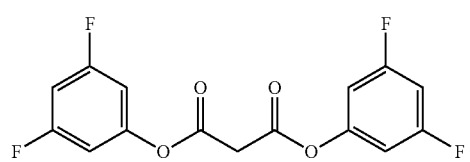
B-12
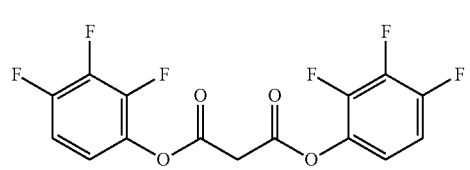
B-13
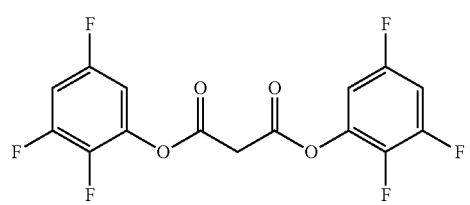
B-14
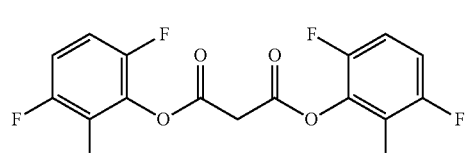
B-15
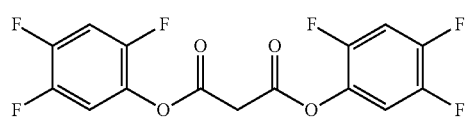
B-16
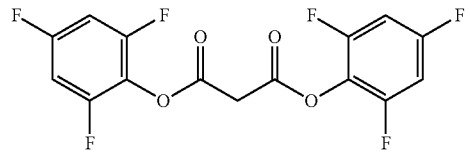
B-17
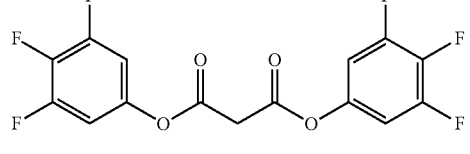
B-18
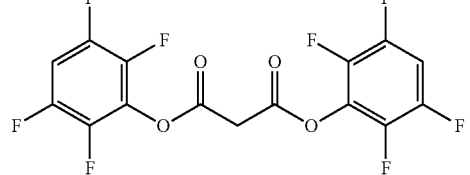
-continued
B-19
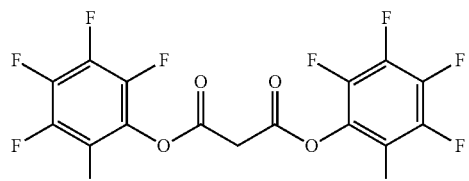
B-20
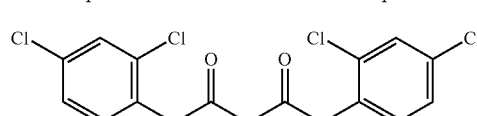
B-21
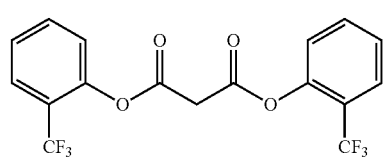
B-22
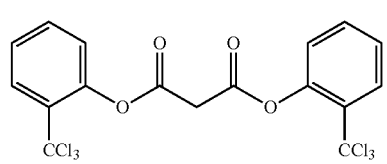
B-23
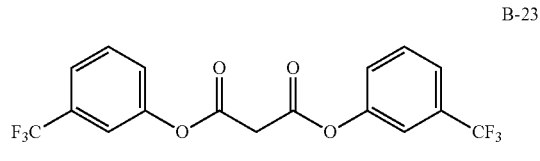
B-24
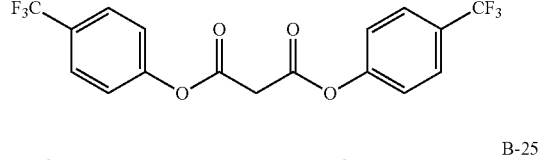
B-25
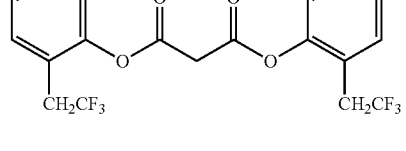
B-26
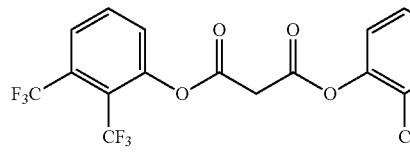
B-27
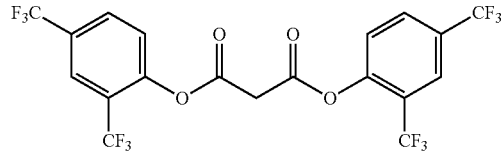

-continued
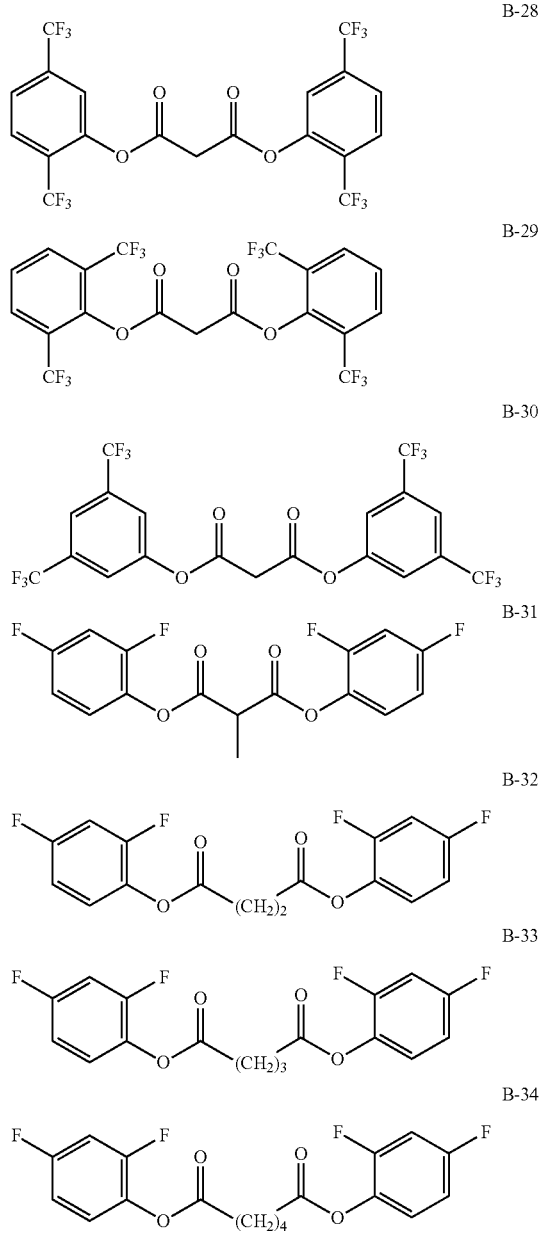
(ii) When Y is a group S(=O)$_2$, the following compounds are preferred.
[Chem. 18]
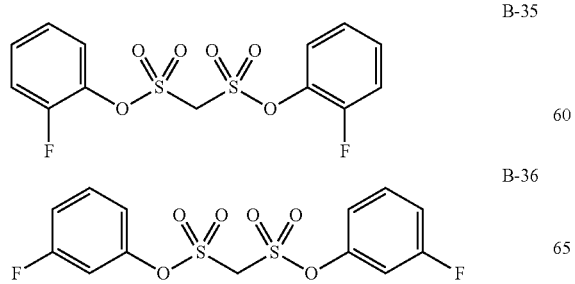
-continued
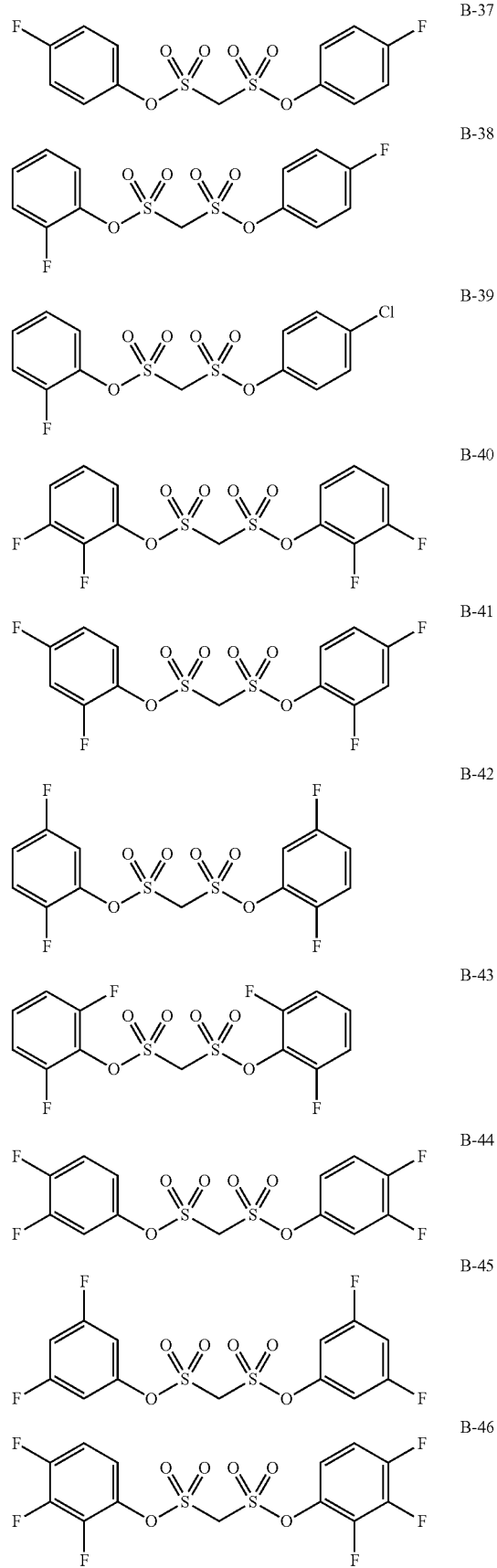

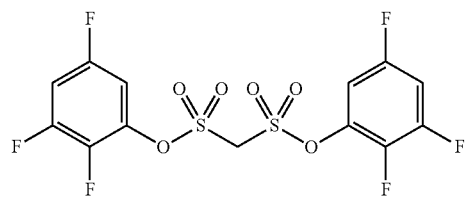
B-47
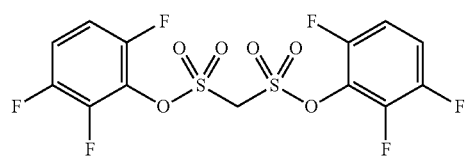
B-48
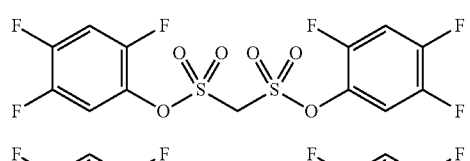
B-49
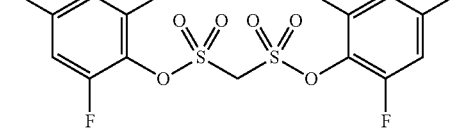
B-50
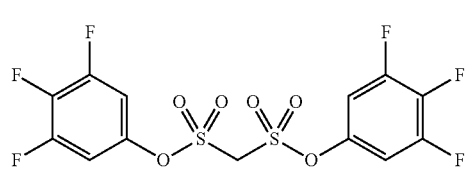
B-51
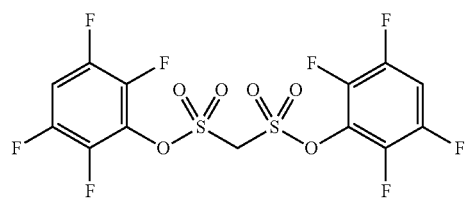
B-52
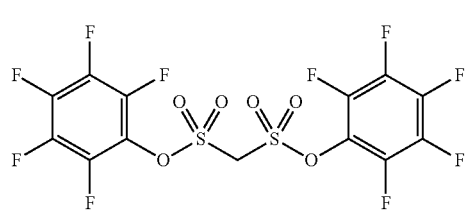
B-53
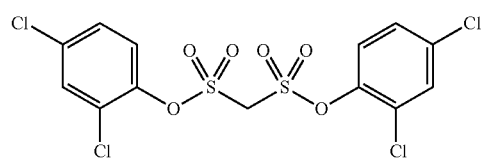
B-54
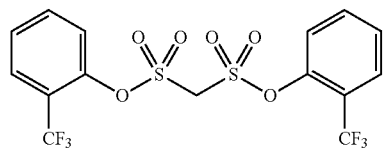
B-55
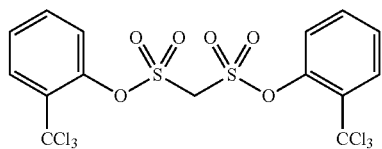
B-56
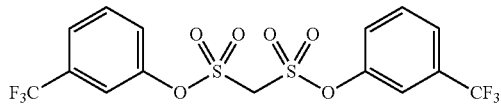
B-57
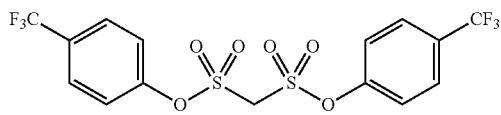
B-58
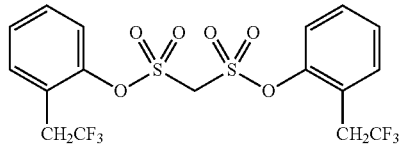
B-59
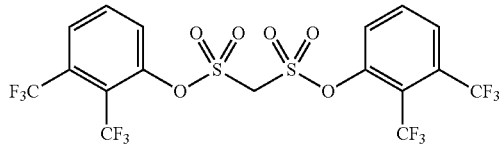
B-60
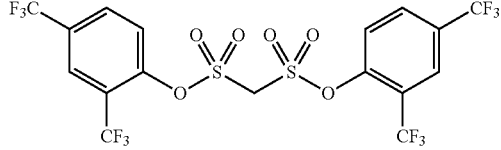
B-61
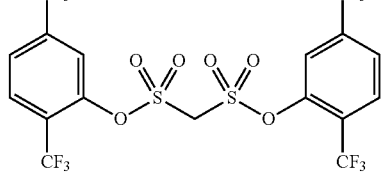
B-62
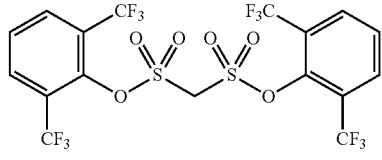
B-63
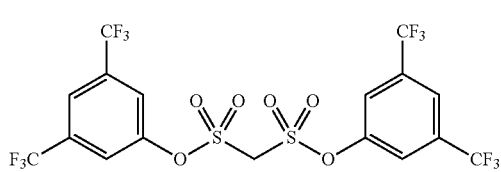
B-64

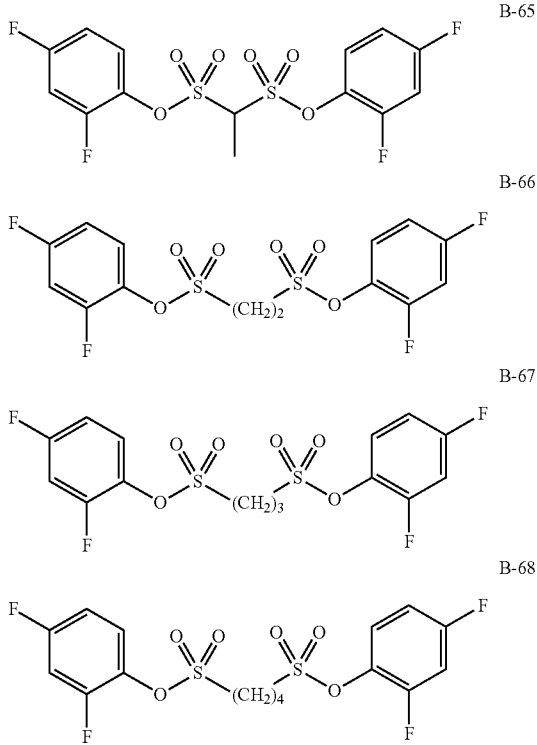

Of the above, preferred are one or more selected from the compounds having any of the above-mentioned structures B-6 to B-17, B-19, B-25, B-40 to B-51, B-53, B-55, and B-66 to B-68; and more preferred are one or more selected from bis(2,4-difluorophenyl) malonate (structural formula B-7), bis(2,4,6-trifluorophenyl) malonate (structural formula B-16), bis(2,3-difluorophenyl)methanedisulfonate (structural formula B-40), bis(2,4-difluorophenyl)methanedisulfonate (structural formula B-41), bis(2,5-difluorophenyl) methanedisulfonate (structural formula B-42), bis(2,6-difluorophenyl)methanedisulfonate (structural formula B-43), bis(3,4-difluorophenyl)methanedisulfonate (structural formula B-44), bis(3,5-difluorophenyl) methanedisulfonate (structural formula B-45), bis(2,3,4-trifluorophenyl) methanedisulfonate (structural formula B-46), bis(2,3,5-trifluorophenyl)methanedisulfonate (structural formula B-47), bis(2,3,6-trifluorophenyl)methanedisulfonate (structural formula B-48), bis(2,4,5-trifluorophenyl)methanedisulfonate (structural formula B-49), bis(2,4,6-trifluorophenyl) methanedisulfonate (structural formula B-50), and bis(3,4,5-trifluorophenyl)methanedisulfonate (structural formula B-51).

The nonaqueous electrolytic solution of the second aspect of the present invention contains, as the compound represented by the general formula (III), one or more selected from the above-mentioned specific examples or preferred examples in an amount of from 0.001 to 10% by mass. When the content is at most 10% by mass, then the risk of excessive formation of a surface film on the electrode to worsen low-temperature properties could be low; and when at least 0.001% by mass, then the surface film formation would be sufficient and the effect of improving high-temperature storage properties could be improved. The content is more preferably at least 0.05% by mass of the nonaqueous electrolytic solution, even more preferably at least 0.2% by mass, and its upper limit is preferably at most 8% by mass, more preferably at most 5% by mass, even more preferably at most 2% by mass.

In the nonaqueous electrolytic solution of the second aspect of the present invention, combining the compound represented by the above-mentioned general formula (III) with the nonaqueous solvent, electrolyte salt and other additives to be mentioned below exhibits a specific effect of synergistically improving electrochemical characteristics in a broad temperature range.

[Nonaqueous Solvent]

The nonaqueous solvent for use in the nonaqueous electrolytic solutions of the present invention, especially that of the first and second aspects of the present invention includes cyclic carbonates, linear esters, lactones, ethers, and amides. Preferably, the solvent contains only a cyclic carbonate or both a cyclic carbonate and a linear ester.

The term "linear ester" is used here as a concept including linear carbonates and linear carboxylates.

Examples of the cyclic carbonates include ethylene carbonate (EC), propylene carbonate (PC), 1,2-butylene carbonate, 2,3-butylene carbonate, 4-fluoro-1,3-dioxolan-2-one (FEC), trans or cis-4,5-difluoro-1,3-dioxolan-2-one (hereinafter the two are collectively called "DFEC"), vinylene carbonate (VC), and vinylethylene carbonate (VEC).

Of those, preferred is use of at least one of a cyclic carbonate having an unsaturated bond, such as a carbon-carbon double bond and a carbon-carbon triple bond and a cyclic carbonate having a fluorine atom, as markedly improving low-temperature load properties after charge and storage at high temperature; and more preferred is use of both a cyclic carbonate having an unsaturated bond, such as a carbon-carbon double bond and a carbon-carbon triple bond and a cyclic carbonate having a fluorine atom. As the cyclic carbonate having a carbon-carbon double bond, more preferred are VC and VEC; and as the cyclic carbonate having a fluorine atom, more preferred are FEC and DFEC.

The content of the carbon-carbon double bond-containing cyclic carbonate is preferably at least 0.07% by volume relative to the total volume of the nonaqueous solvent, more preferably at least 0.2% by volume, even more preferably at least 0.7% by volume, and the upper limit thereof is preferably at most 7% by volume, more preferably at most 4% by volume, even more preferably at most 2.5% by volume. The range is preferred as capable of markedly improving the stability of the surface film during storage at high temperature without deteriorating the Li ion permeability at low temperature.

The content of the fluorine atom-containing cyclic carbonate is preferably at least 0.07% by volume relative to the total volume of the nonaqueous solvent, more preferably at least 4% by volume, even more preferably at least 7% by volume, and the upper limit thereof is preferably at most 35% by volume, more preferably at most 25% by volume, even more preferably at most 15% by volume. The range is preferred as capable of markedly improving the stability of the surface film during storage at high temperature without deteriorating the Li ion permeability at low temperature.

Preferably, the nonaqueous solvent contains one or two selected from ethylene carbonate and propylene carbonate, as the resistance of the surface film formed on electrodes can be reduced. Preferably, the content of ethylene carbonate and/or propylene carbonate is at least 3% by volume relative to the total volume of the nonaqueous solvent, more preferably at least 5% by volume, even more preferably at least 7% by volume, and its upper limit is preferably at most 45% by volume, more preferably at most 35% by volume, even more preferably at most 25% by volume.

One kind of those solvents may be used, but using two or more different kinds thereof as combined is preferred as further improving electrochemical characteristics in a broad temperature range. Even more preferably, three or more different kinds are combined. Preferred combinations of the cyclic carbonates include EC and PC; EC and VC; PC and VC; VC and FEC; EC and FEC; PC and FEC; FEC and DFEC; EC and DFEC; PC and DFEC; VC and DFEC; VEC and DFEC; EC and PC and VC; EC and PC and FEC; EC and VC and FEC; EC and VC and VEC; PC and VC and FEC; EC and VC and DFEC; PC and VC and DFEC; EC and PC and VC and FEC; EC and PC and VC and DFEC; etc. Of those combinations, more preferred combinations are EC and VC; EC and FEC; PC and FEC; EC and PC and VC; EC and PC and FEC; EC and VC and FEC; PC and VC and FEC; EC and PC and VC and FEC; etc.

As the linear esters, preferably mentioned are one or more selected from asymmetric linear carbonates selected from methyl ethyl carbonate (MEC), methyl propyl carbonate (MPC), methyl isopropyl carbonate (MIPC), methyl butyl carbonate and ethyl propyl carbonate; symmetric linear carbonates selected from dimethyl carbonate (DMC), diethyl carbonate (DEC), dipropyl carbonate and dibutyl carbonate; pivalates selected from methyl pivalate, ethyl pivalate and propyl pivalate; and linear carboxylates selected from methyl propionate, ethyl propionate, methyl acetate and ethyl acetate.

Of the above-mentioned linear esters, preferred are one or more methyl group-having linear esters selected from methyl ethyl carbonate, methyl propyl carbonate, methyl isopropyl carbonate, methyl butyl carbonate, dimethyl carbonate, methyl propionate, methyl acetate and ethyl acetate; and more preferred are one or more of methyl group-having linear carbonates, such as methyl ethyl carbonate (MEC), methyl propyl carbonate (MPC), methyl isopropyl carbonate (MIPC), methyl butyl carbonate and dimethyl carbonate (DMC).

Preferably, two or more different types of linear carbonates are used here. More preferably, a combination of a symmetric linear carbonate and an asymmetric linear carbonate is used; and even more preferably, the content of the symmetric linear carbonate is larger than that of the asymmetric linear carbonate.

Not specifically defined, the content of the linear ester is preferably within a range of from 60 to 90% by volume relative to the total volume of the nonaqueous solvent. When the content is at least 60% by volume, the effect of lowering the viscosity of the nonaqueous electrolytic solution is sufficiently exhibited; and when at most 90% by volume, the electric conductivity of the nonaqueous electrolytic solution is sufficiently increased to improve electrochemical characteristics in a broad temperature range. For these reasons, the above-mentioned range is preferred here.

The ratio by volume of the symmetric linear carbonate to the linear carbonate is preferably at least 51% by volume, more preferably at least 55% by volume, and its upper limit is preferably at most 95% by volume, more preferably at most 85% by volume. Especially preferably, the symmetric linear carbonate for use herein contains dimethyl carbonate. Also preferably, the asymmetric linear carbonate for use herein has a methyl group, and especially preferred is use of methyl ethyl carbonate here.

The above-mentioned embodiments are preferred as remarkably improving electrochemical characteristics in a broad temperature range.

The ratio of the cyclic carbonate to the linear ester, cyclic carbonate/linear ester (by volume) is preferably from 10/90 to 45/55, more preferably from 15/85 to 40/60, even more preferably from 20/80 to 35/65, from the viewpoint of improving electrochemical characteristics in a broad temperature range.

As other nonaqueous solvents preferred for use herein, there are mentioned cyclic ethers, such as tetrahydrofuran, 2-methyltetrahydrofuran, 1,3-dioxolane, 1,3-dioxane, 1,4-dioxane, etc.; linear ethers, such as 1,2-dimethoxyethane, 1,2-diethoxyethane, 1,2-dibutoxyethane, etc.; amides, such as dimethylformamide, etc.; sulfones, such as sulfolane, etc.; lactones, such as γ-butyrolactone, γ-valerolactone, α-angelicalactone, etc.

The nonaqueous solvent is usually used in a mixture in order to achieve the desired physical properties. Preferred examples of the combination thereof include the combination of cyclic carbonate and linear carbonate, the combination of cyclic carbonate and linear carboxylic ester, the combination of cyclic carbonate, linear carbonate and lactone, the combination of cyclic carbonate, linear carbonate and ether, and the combination of cyclic carbonate, linear carbonate and linear carboxylic ester.

For the purpose of markedly improving electrochemical characteristics in a broad temperature range, it is desirable that any other additive is further added to the nonaqueous electrolytic solution.

As preferred examples of the other additives, further mentioned are phosphates such as trimethyl phosphate, tributyl phosphate, trioctyl phosphate, etc.; nitriles such as acetonitrile, propionitrile, succinonitrile, glutaronitrile, adiponitrile, pimelonitrile, etc.; isocyanates such as tetramethylene diisocyanate, hexamethylene diisocyanate, octamethylene diisocyanate, etc.; S=O group-containing compounds selected from sultones such as 1,3-propanesultone, 1,3-butanesultone, 2,4-butanesultone, 1,4-butanesultone, etc., cyclic sulfites, such as ethylene sulfite, hexahydrobenzo[1,3,2]dioxathiolane-2-oxide (also referred to as 1,2-cyclohexanediol cyclic sulfite), 5-vinyl-hexahydro1,3,2-benzodioxathiol-2-oxide, etc., sulfonates such as 2-propynyl methanesulfonate, butane-1,4-diyl dimethanesulfonate, butyne-1,4-diyl dimethanesulfonate, pentane-1,5-diyl dimethanesulfonate, propane-1,2-diyl dimethanesulfonate, butane-2,3-diyl dimethanesulfonate, methylenemethane disulfonate, 2-trifluoromethylphenyl methanesulfonate, pentafluorophenyl methanesulfonate, methylenemethane disulfonate etc., and vinyl sulfones such as divinyl sulfone, 1,2-bis(vinylsulfonyl) ethane, bis(2-vinylsulfonylethyl) ether, etc.; linear carboxylic acid anhydrides such as acetic anhydride, propionic anhydride, etc.; cyclic acid anhydrides such as succinic anhydride, maleic anhydride, glutaric anhydride, itaconic anhydride, 3-sulfo-propionic acid anhydride, etc.; cyclic phosphazenes such as methoxypentafluorocyclotriphosphazene, ethoxypentafluorocyclotriphosphazene, phenoxypentafluorocyclotriphosphazene, ethoxypentafluorocyclotetraphosphazene, etc.; aromatic compound having a branched alkyl group such as cyclohexylbenzene, fluorocyclohexylbenzene compound (1-fluoro-2-cyclohexylbenzene, 1-fluoro-3-cyclohexylbenzene, and 1-fluoro-4-cyclohexylbenzene), tert-butylbenzene, tert-amylbenzene, 1-fluoro-4-tert-bytylbenzene, etc.; aromatic compounds such as biphenyl, terphenyl (o-, m-, p-form), diphenyl ether, fluorobenzene, difluorobenzene (o-, m-, p-form), anisole, 2,4-difluoroanisole or partial hydrides of terphenyl (1,2-dicyclohexylbenzene, 2-phenylbicyclohexyl, 1,2-diphenylcyclohexane, o-cyclohexylbiphenyl), etc.

[Electrolyte Salt]

As the electrolyte salt for use in the present invention, especially in the first and second aspects of the present inventions, preferably mentioned are the following lithium salts and onium salts.

(Lithium Salt)

The lithium salt includes inorganic lithium salts, such as $LiPF_6$, $LiPO_2F_2$, $Li_2PO_3F$, $LiBF_4$, $LiClO_4$, $LiSO_3F$, etc.; linear fluoroalkyl group-having lithium salts, such as $LiN(SO_2F)_2$, $LiN(SO_2CF_3)_2$, $LiN(SO_2C_2F_5)_2$, $LiCF_3SO_3$, $LiC(SO_2CF_3)_3$, $LiPF_4(CF_3)_2$, $LiPF_3(C_2F_5)_3$, $LiPF_3(CF_3)_3$, $LiPF_3(iso-C_3F_7)_3$, $LiPF_5(iso-C_3F_7)$, etc.; cyclic fluoroalkylene chain-having lithium salts, such as $(CF_2)_2(SO_2)_2NLi$, $(CF_2)_3(SO_2)_2NLi$, etc.; and lithium salts with an oxalate complex as the anion therein, such as lithium bis[oxalate-O,O']borate, lithium difluoro[oxalate-O,O']borate, lithium difluorobis[oxalate-O,O']phosphate, lithium tetrafluoro[oxalate-O,O']phosphate, etc. One or more of these as combined may be used here. Of those, preferred is at least one selected from $LiPF_6$, $LiPO_2F_2$, $Li_2PO_3F$, $LiBF_4$, $LiSO_3F$, $LiN(SO_2CF_3)_2$ and $LiN(SO_2C_2F_5)_2$, $LiN(SO_2F)_2$, lithium difluorobis[oxalate-O,O']phosphate and lithium tetrafluoro[oxalate-O,O']phosphate; and more preferred is at least one selected from $LiPF_6$, $LiPO_2F_2$, $LiBF_4$, $LiN(SO_2CF_3)_2$, $LiN(SO_2F)_2$, and lithium difluorobis[oxalate-O,O']phosphate. The concentration of the lithium salt is, in general, preferably at least 0.3 M relative to the above-mentioned nonaqueous solvent, more preferably at least 0.7 M, even more preferably at least 1.1 M. The upper limit of the content is preferably at most 2.5 M, more preferably at most 2.0 M, even more preferably at most 1.6 M.

A preferred combination of these lithium salts to be contained in the nonaqueous electrolytic solution comprises $LiPF_6$ and contains at least one lithium salt selected from $LiPO_2F_2$, $LiBF_4$, $LiN(SO_2CF_3)_2$, $LiN(SO_2F)_2$ and lithium difluorobis[oxalate-O,O']phosphate.

The proportion of the lithium salt except $LiPF_6$ in the nonaqueous solvent is preferably at least 0.001 M, as readily exhibiting the effect of improving electrochemical characteristics in a broad temperature range, and is also preferably at most 0.5 M as free from the risk of lowering the effect of improving electrochemical characteristics in a broad temperature range. More preferably, the proportion is at least 0.01 M, even more preferably at least 0.03 M, and most preferably at least 0.04 M. The upper limit of the proportion is preferably at most 0.4 M, more preferably at most 0.2 M.

(Onium Salt)

Preferred examples of the onium salt are various salts of a combination of an onium cation and an anion mentioned below.

As specific examples of the onium cation, preferably mentioned are one or more selected from a tetramethylammonium cation, an ethyltrimethylammonium cation, a diethyldimethylammonium cation, a triethylmethylammonium cation, a tetraethylammonium cation, an N,N-dimethylpyrrolidinium cation, an N-ethyl-N-methylpyrrolidinium cation, an N,N-diethylpyrrolidinium cation, a spiro-(N,N')-bipyrrolidinium cation, an N,N'-dimethylimidazolinium cation, an N-ethyl-N'-methylimidazolinium cation, an N,N'-diethylimidazolinium cation, an N,N'-dimethylimidazolinium cation, an N-ethyl-N'-methylimidazolinium cation, an N,N'-diethylimidazolinium cation, etc.

Preferred examples of the anion include one or more selected from a $PF_6$ anion, a $BF_4$ anion, a $ClO_4$ anion, an $AsF_6$ anion, a $CF_3SO_3$ anion, an $N(CF_3SO_2)_2$ anion, an $N(C_2F_5SO_2)_2$ anion, etc.

One alone or two or more different types of these onium salts may be used here either singly or as combined.

[Production of Nonaqueous Electrolytic Solution]

The nonaqueous electrolytic solutions of the present invention, especially that of the first and second aspects of the present invention may be produced, for example, by mixing the above-mentioned nonaqueous solvents, adding the above-mentioned electrolyte salt, and further adding thereto the organic phosphorus compound represented by the above-mentioned general formula (I), (II) or (III) to the resulting nonaqueous electrolytic solution.

Preferably, the nonaqueous solvent to be used and the compound to be added to the nonaqueous electrolytic solution are previously purified to reduce as much as possible the content of impurities therein within a range not extremely detracting from the productivity.

The nonaqueous electrolytic solutions of the present invention, especially that of the first and second aspects of the present invention can be used in the first to fourth energy storage devices mentioned below, in which as the nonaqueous electrolyte, not only a liquid one but also a gelled one may be used. Further, the nonaqueous electrolytic solution of the present invention can also be used for solid polymer electrolytes. Especially preferably, the solution is used in the first energy storage device where a lithium salt is used as the electrolyte salt (that is, for lithium batteries), or in the fourth energy storage device (that is, for lithium ion capacitors); and more suitably, the solution is used for lithium batteries, even more preferably for lithium secondary batteries.

[First Energy Storage Device (Lithium Battery)]

The lithium battery in this specification means a generic name for a lithium primary battery and a lithium secondary battery. In this specification, the term, lithium secondary battery is used as a concept that includes so-called lithium ion secondary batteries. The lithium battery of the present invention comprises a positive electrode, a negative electrode, and the above-mentioned nonaqueous electrolytic solution of an electrolyte salt dissolved in a nonaqueous solvent. The other constitutive members, such as the positive electrode, the negative electrode and others than the nonaqueous electrolytic solution are not specifically defined for use herein.

For example, as the positive electrode active material for lithium secondary batteries, usable is a complex metal oxide of lithium and one or more selected from cobalt, manganese and nickel. One alone or two or more of these positive electrode active materials may be used here either singly or as combined.

The lithium complex metal oxide includes, for example, one or more selected from $LiCoO_2$, $LiMn_2O_4$, $LiNiO_2$, $LiCO_{1-x}Ni_xO_2(0.01<x<1)$, $LiCO_{1/3}Ni_{1/3}Mn_{1/3}O_2$, $LiNi_{1/2}Mn_{3/2}O_4$, $LiCo_{0.98}Mg_{0.02}O_2$, etc. Also usable here is a combination of $LiCoO_2$ and $LiMn_2O_4$, a combination of $LiCoO_2$ and $LiNiO_2$, or a combination of $LiMn_2O_4$ and $LiNiO_2$.

For improving the safety in overcharging and the cycle properties of the batteries, or for enabling the use thereof at a charge potential of 4.3 V or more, a part of the lithium complex metal oxide may be substituted with any other element. For example, a part of cobalt, manganese and nickel may be substituted with at least one or more elements of Sn, Mg, Fe, Ti, Al, Zr, Cr, V, Ga, Zn, Cu, Bi, Mo, La, etc.; or a part of O may be substituted with S or F; or the oxide may be coated with a compound containing any of such other elements.

Of those, preferred are lithium complex metal oxides, such as one or more selected from $LiCoO_2$, $LiMn_2O_4$ and $LiNiO_2$, with which the charge potential of the positive electrode in a fully-charged state could be 4.3 V or more based on Li; and more preferred are lithium complex metal oxides, such as solid solutions of $LiCo_{1-x}M_xO_2$ (where M is one or more elements selected from Sn, Mg, Fe, Ti, Al, Zr, Cr, V, Ga, Zn and Cu; $0.001 \leq x \leq 0.05$), $LiCo_{1/3}Ni_{1/3}Mn_{1/3}O_2$, $LiNi_{1/2}Mn_{3/2}O_4$, $Li_2MnO_3$ and $LiMO_2$ (where M is a transition metal, such as Co, Ni, Mn, Fe, etc.) that can be used at 4.4 V or more. When the lithium complex metal oxide capable of acting at a high charge voltage is used, then the electrochemical characteristics in a broad temperature range may often worsen owing to the reaction of the oxide with the electrolytic solution in charging; however, in the lithium secondary battery of the present invention, the electrochemical characteristics can be prevented from worsening.

Especially, in the case of a positive electrode containing Mn, there is a tendency that the elution of Mn ion from the positive electrode increases the resistance of the battery, thereby deteriorating that electrochemical characteristics in a broad temperature range. It is preferred that the lithium secondary batteries of the present invention can restrain the electrochemical characteristics from being deteriorated.

Further, as the positive electrode active material, also usable are lithium-containing olivine-type phosphates. Especially preferred are lithium-containing olivine-type phosphates containing at least one selected from iron, cobalt, nickel and manganese. Specific examples thereof include one or more selected from $LiFePO_4$, $LiCoPO_4$, $LiNiPO_4$, $LiMnPO_4$, etc.

The lithium-containing olivine-type phosphates may be partly substituted with any other element. For example, a part of iron, cobalt, nickel, and manganese therein may be substituted with at least one element selected from Co, Mn, Ni, Mg, Al, B, Ti, V, Nb, Cu, Zn, Mo, Ca, Sr, W, and Zr; or the phosphates may be coated with a compound containing any of these other elements or with a carbon material. Among these, preferred are $LiFePO_4$ and $LiMnPO_4$.

Further, the lithium-containing olivine-type phosphate may be combined with, for example, the above-mentioned positive electrode active materials.

For the positive electrode for lithium primary batteries, there are mentioned oxides or chalcogen compounds of one or more metal elements, such as CuO, $Cu_2O$, $Ag_2O$, $Ag_2CrO_4$, CuS, $CuSO_4$, $TiO_2$, $TiS_2$, $SiO_2$, SnO, $V_2O_5$, $V_6O_{12}$, $VO_x$, $Nb_2O_5$, $Bi_2O_3$, $Bi_2Pb_2O_5$, $Sb_2O_3$, $CrO_3$, $Cr_2O_3$, $MoO_3$, $WO_3$, $SeO_2$, $MnO_2$, $Mn_2O_3$, $Fe_2O_3$, FeO, $Fe_3O_4$, $Ni_2O_3$, NiO, $CoO_3$, CoO, etc.; sulfur compounds, such as $SO_2$, $SOCl_2$, etc.; carbon fluorides (graphite fluoride) represented by a general formula $(CF_x)_n$, etc. Of those, preferred are one or more selected from $MnO_2$, $V_2O_5$, fluorographite, etc.

Not specifically defined, the electroconductive agent of the positive electrode may be any electron-conductive material not undergoing chemical change. For example, it includes graphites, such as natural graphite (flaky graphite, etc.), artificial graphite, etc.; carbon blacks, such as acetylene black, Ketjen black, channel black, furnace black, lamp black, thermal black, etc. Graphites and carbon blacks may be combined suitably. The amount of the electroconductive agent to be added to the positive electrode mixture is preferably from 1 to 10% by mass, more preferably from 2 to 5% by mass.

The positive electrode may be formed by mixing the above-mentioned positive electrode active material with an electroconductive agent, such as acetylene black, carbon black or the like, and with a binder, such as polytetrafluoroethylene (PTFE), polyvinylidene fluoride (PVDF), styrene/butadiene copolymer (SBR), acrylonitrile/butadiene copolymer (NBR), carboxymethyl cellulose (CMC), ethylene/propylene/diene terpolymer or the like, then adding thereto a high-boiling point solvent, such as 1-methyl-2-pyrrolidone or the like, and kneading them to give a positive electrode mixture, thereafter applying the positive electrode mixture onto an aluminium foil or a stainless lath plate or the like serving as a collector, and drying and shaping it under pressure, and then heat-treating it in vacuum at a temperature of from 50° C. to 250° C. or so for about 2 hours.

The density of the part except the collector of the positive electrode may be generally at least 1.5 $g/cm^3$, and for further increasing the capacity of the battery, the density is preferably at least 2 $g/cm^3$, more preferably at least 3 $g/cm^3$, even more preferably at least 3.6 $g/cm^3$. The upper limit is preferably at most 4 $g/cm^3$.

As the negative electrode active material for lithium secondary batteries, usable are one or more of lithium metal, lithium alloys, carbon materials capable of absorbing and releasing lithium [graphatizable carbon, non-graphatizable carbon where the lattice (002) spacing is at least 0.37 nm, graphite where the lattice (002) spacing is at most 0.34 nm, etc.], tin (elementary substance), tin compounds, silicon (elementary substance), silicon compounds, lithium titanate compounds, such as $Li_4Ti_5O_{12}$ and the like, either singly or as combined with two or more thereof.

Of those, more preferred is use of high-crystalline carbon materials, such as artificial graphite, natural graphite and the like, in view of the ability thereof to absorb and release lithium ions, and even more preferred is use of a carbon material having a graphite-type crystal structure where the lattice (002) spacing ($d_{002}$) is at most 0.340 nm (nanometers), especially from 0.335 to 0.337 nm.

In particular, preferred here is use of artificial graphite particles having a bulky structure where plural flattened graphite fine particles aggregate or bond together non-parallel to each other, or graphite particles produced through spheroidizing treatment of flaky natural graphite particles by imparting thereto repeated mechanical action, such as compression force, friction force, shear force or the like. Preferably, the ratio of the peak intensity I (110) of the (110) plane of the graphite crystal obtained in X-ray diffractiometry of a negative electrode sheet as formed by pressing so that the density of the part except the collector of the negative electrode could be at least 1.5 $g/cm^3$, to the peak intensity I (004) of the (004) plane thereof, I (110)/I (004) is at least 0.01, since the electrochemical characteristics in a broad temperature range of the battery can be markedly improved. More preferably, the ratio is at least 0.05, even more preferably at least 0.1. On the other hand, when too much processed, then the crystallinity may worsen and the discharge capacity of the battery may lower; and therefore, the upper limit is preferably at most 0.5, more preferably at most 0.3.

Preferably, the high-crystalline carbon material (core material) is coated with a different carbon material that is more low-crystalline than the core material, as further bettering electrochemical characteristics in a broad temperature range. The crystallinity of the carbon material in coating may be confirmed through TEM.

When the high-crystalline carbon material is used, it may readily react with the nonaqueous electrolytic solution in charging to thereby worsen electrochemical characteristics at low temperature or at high temperatures owing to the increase in the interfacial resistance; however, in the lithium secondary battery of the present invention, the electrochemical characteristics in a broad temperature range can be bettered.

The metal compound capable of absorbing and releasing lithium, serving as a negative electrode active material, includes compounds containing at least one metal element of Si, Ge, Sn, Pb, P, Sb, Bi, Al, Ga, In, Ti, Mn, Fe, Co, Ni, Cu, Zn, Ag, Mg, Sr, Ba, etc. These metal compounds may have any morphology of elementary substances, alloys, oxides, nitrides, sulfides, borides, alloys with lithium or the like; but preferred are any of elementary substances, alloys, oxides and alloys with lithium, as capable of increasing the battery capacity. Above all, more preferred are those containing at least one element selected from Si, Ge and Sn, and even more preferred are those containing at least one element selected from Si and Sn, as capable of increasing the battery capacity.

The negative electrode may be formed, using the same electroconductive agent, binder and high-boiling point solvent as in the formation of the above-mentioned positive electrode. These are mixed and kneaded to give a negative electrode mixture, then the negative electrode mixture is applied onto a copper foil or the like serving as a collector, then dried and shaped under pressure, and thereafter heat-treated in vacuum at a temperature of from 50° C. to 250° C. or so for about 2 hours.

The density of the part except the collector of the negative electrode may be generally at least 1.1 g/cm$^3$, and for further increasing the battery capacity, the density is preferably at least 1.5 g/cm$^3$, more preferably at least 1.7 g/cm$^3$. The upper limit is preferably at most 2 g/cm$^3$.

As the negative electrode active material for lithium primary batteries, usable are lithium metal or lithium alloys.

The structure of the lithium battery is not specifically defined. The battery may be a coin-type battery, a cylinder-type battery, a square-shaped battery, a laminate-type battery or the like, each having a single-layered or multi-layered separator.

The separator for the battery is not specifically defined, for which usable is a single-layer or laminate porous film of polyolefin, such as polypropylene, polyethylene or the like, as well as a woven fabric, a nonwoven fabric, etc.

The lithium secondary battery of the present invention has excellent electrochemical characteristics in a broad temperature range even when the final charging voltage is 4.2 V or more, especially 4.3 V or more, and further, the electrochemical characteristics of the battery are still good even at 4.4 V or more. The final discharging voltage could be generally 2.8 V or more, further 2.5 V or more; however, the final discharging voltage of the lithium secondary battery of the present invention could be 2.0 V or more. The current value is not specifically defined, but in general, the battery is used within a range of from 0.1 to 30 C. The lithium battery of the present invention can be charged/discharged at −40 to 100° C., preferably at −10 to 80° C.

In the present invention, as a countermeasure against the increase in the internal pressure of the lithium battery, there may be employed a method of providing a safety valve in the battery cap or a method of forming a cutout in the battery component, such as the battery can, the gasket or the like. In addition, as a safety countermeasure against overcharging, a current cut-off mechanism capable of detecting the internal pressure of the battery to cut off the current may be provided in the battery cap.

[Second Energy Storage Device (Electric Double-layer Capacitor)]

This is an energy storage device that stores energy by utilizing the electric double layer capacitance in the interface between the electrolytic solution and the electrode therein. One example of the present invention is an electric double layer capacitor. The most typical electrode active material to be used in the energy storage device is active carbon. The double layer capacitance increases almost in proportion to the surface area.

[Third Energy Storage Device]

This is an energy storage device that stores energy by utilizing the doping/dedoping reaction of the electrode therein. As the electrode active material for use in the energy storage device, there may be mentioned metal oxides, such as ruthenium oxide, iridium oxide, tungsten oxide, molybdenum oxide, copper oxide, etc.; π-conjugated polymers, such as polyacene, polythiophene derivatives, etc. The capacitor that uses the electrode active material of the type enables energy storage along with the doping/dedoping reaction at the electrode therein.

[Fourth Energy Storage Device (Lithium Ion Capacitor)]

This is an energy storage device that stores energy by utilizing the lithium ion intercalation into the carbon material, such as graphite or the like of the negative electrode therein. This may be referred to as a lithium ion capacitor (LIC). As the positive electrode, for example, there may be mentioned one that utilizes the electric double layer between the active carbon electrode and the electrolytic solution therein, or one that utilizes the doping/dedoping reaction of the π-conjugated polymer electrode therein. The electrolytic solution contains at least a lithium salt, such as LiPF$_6$ or the like.

[Cycloalkanedisulfonate Compound]

The cycloalkanedisulfonate compound of the present invention is represented by the following general formula (II-1):

[Chem. 19]

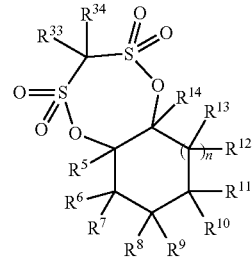

(II-1)

(In the formula, $R^{33}$ and $R^{34}$ each independently represent a hydrogen atom, a halogen atom, or an alkyl group having from 1 to 4 carbon atoms; and $R^5$ to $R^{14}$ each independently represent a hydrogen atom, an alkyl group having from 1 to 6 carbon atoms, an alkenyl group having from 2 to 6 carbon atoms, an alkynyl group having from 2 to 6 carbon atoms, an aryl group having from 6 to 12 carbon atoms, or an alkoxy group having from 1 to 6 carbon atoms, they may bond to each other to form a ring structure, and the hydrogen atom thereof may be substituted with a halogen atom. n indicates an integer of from 0 to 3.)

Specific examples of $R^{33}$ and $R^{34}$ in the general formula (II-1) include a hydrogen atom, a fluorine atom, a chlorine atom, a bromine atom, a methyl group, an ethyl group, an n-propyl group, an n-butyl group, an n-pentyl group, an n-hexyl group, an iso-propyl group, a sec-butyl group, a tert-butyl group, etc. Of those, preferred are a hydrogen atom, a fluorine atom, a methyl group and an ethyl group; and more preferred is a hydrogen atom.

n is preferably 0 or 1, more preferably 1.

Specific examples of $R^5$ to $R^{14}$ in the general formula (II-1) include a hydrogen atom, an alkyl group, such as a methyl group, an ethyl group, an n-propyl group, an n-butyl group, an n-pentyl group, an n-hexyl group, an iso-propyl group, a sec-butyl group, a tert-butyl group, etc.; an alkenyl group, such as an ethenyl group, a 2-propenyl group, a 2-butenyl group, a 3-butenyl group, a 4-pentenyl group, a 5-hexenyl group, a 2-methyl-2-propenyl group, a 3-methyl-2-butenyl group, etc.; an alkynyl group, such as a 2-propynyl group, a 3-butynyl group, a 4-pentynyl group, a 5-hexynyl group, a 2-methyl-2-propynyl group, a 2,2-dimethyl-2-propynyl group, etc.; an aryl group such as a phenyl group, a 2-methylphenyl group, a 3-methylphenyl group, a 4-methylphenyl group, a 4-tert-butylphenyl group, a 2,4,6-trimethylphenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 2,4,6-trifluorophenyl group, a pentafluorophenyl group, a 4-trifluoromethylphenyl group, etc. Of those, preferably, $R^5$ to $R^{14}$ each independently represent a hydrogen atom, an alkyl group having from 1 to 4 carbon atoms, an alkenyl group having from 2 to 4 carbon atoms, or an alkynyl group having from 2 to 4 carbon atoms, more preferably a hydrogen atom, an alkyl group having from 2 to 4 carbon atoms, or an alkenyl group having from 2 to 4 carbon atoms, even more preferably a hydrogen atom, a methyl group, an ethyl group, an ethenyl group or a 2-propenyl group, still more preferably a hydrogen atom, a methyl group or an ethenyl group.

Specific examples and preferred examples of the cycloalkanedisulfonate compound represented by the general formula (II-1) are the same as those of the compound represented by the general formula (II).

The compound represented by the general formula (II-1) of the present invention can be produced according to (A) a method of transesterifying an alkanedisulfonyl dihalide compound with the corresponding diol compound in the presence or absence of a solvent and in the presence or absence of a base; however, the production method is not limited to the method (A).

In the method (A), the amount of the diol compound to be used is preferably from 0.8 to 15 mols relative to 1 mol of the alkanedisulfonyl dihalide compound, more preferably from 0.9 to 10 mols, even more preferably from 1 to 5 mols.

The alkanedisulfonyl dihalide compound to be used includes methanedisulfonyl dichloride, methanedisulfonyl dibromide, fluoromethanesulfonyl dichloride, ethane-1,1-disulfonyl dichloride, etc.

The diol compound to be used includes cyclopentane-1,2-diol, cyclohexane-1,2-diol, cycloheptane-1,2-diol, cyclooctane-1,2-diol, 2-fluorophenyl, 3-fluorophenol, 4-fluorophenol, 4-propylcyclohexane-1,2-diol, 3-vinylcyclohexane-1,2-diol, 4-vinylcyclohexane-1,2-diol, 4-(1-propen-2-yl)cyclohexane-1,2-diol, 3-isopropylcyclohexane-1,2-diol, 4-isopropylcyclohexane-1,2-diol, 3-isopropyl-6-methylcyclohexane-1,2-diol, 3-methoxycyclohexane-1,2-diol, 3-methoxy-3-methyl-6-(1-propen-2-yl)cyclohexane-1,2-diol, etc.

In the method (A), the reaction may go on with no solvent, but a solvent inert to the reaction may be used. The solvent to be used includes aliphatic hydrocarbons such as heptane, cyclohexane, etc.; halogenohydrocarbons such as dichloromethane, dichloroethane, etc.; aromatic hydrocarbons such as toluene, xylene, etc.; halogenoaromatic hydrocarbons such as chlorobenzene, fluorobenzene, etc.; ethers such as diisopropyl ether, dioxane, dimethoxyethane, etc.; esters such as ethyl acetate, butyl acetate, dimethyl carbonate, diethyl carbonate, etc.; nitriles such as acetonitrile, propionitrile, etc.; sulfoxides such as dimethyl sulfoxide, sulfolane, etc.; amides such as N,N-dimethylformamide, N,N-dimethylacetamide, etc.; and their mixtures. Of those, preferred are aliphatic or aromatic hydrocarbons and esters, such as heptane, cyclohexane, toluene, ethyl acetate, dimethyl carbonate, etc.

The amount of the solvent to be used is preferably from 0 to 30 parts by mass relative to 1 part by mass of the alkanedisulfonyl dihalide compound, more preferably from 1 to 10 parts by mass.

In the method (A), the reaction may go on with no base, but the presence of a base therein is preferred as promoting the reaction. As the base, any of an inorganic base or an organic base may be used.

The inorganic base includes potassium carbonate, sodium carbonate, calcium hydroxide and calcium oxide. The organic base includes a linear or branched aliphatic tertiary amine, a substituted or unsubstituted imidazole, pyridine or pyrimidine. Of those, preferred are trialkylamines such as trimethylamine, triethylamine, tripropylamine, tributylamine, diisopropylethylamine, etc.; pyridines such as pyridine, N,N-dimethylaminopyridine, etc.

The amount of the base to be used is preferably from 1.6 to 10 mols relative to 1 mol of the alkanedisulfonyl dihalide compound, more preferably from 2 to 6 mols, even more preferably from 2 to 3 mols.

In the method (A), the lower limit of the reaction temperature is preferably not lower than −20° C., more preferably not lower than −10° C., from the viewpoint of not lowering the reactivity. From the viewpoint of preventing any side reaction and decomposition of products, the upper limit of the reaction temperature is preferably not higher than 100° C., more preferably not higher than 80° C.

The reaction time may be suitably changed depending on the reaction temperature and the scale; however, when the reaction time is too short, then unreacted matters may remain, but on the contrary, when the reaction time is too long, then there may occur a risk of decomposition of reaction products and side reaction. Therefore, preferably, the reaction time is from 0.1 to 12 hours, more preferably from 0.2 to 6 hours.

[Alkanedisulfonate Compound]

The alkanedisulfonate compound of the present invention is represented by the following general formula (III-1):

[Chem. 20]

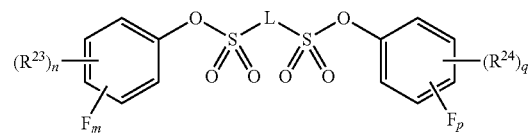

(III-1)

(In the formula, $R^{23}$ and $R^{24}$ each independently represent a fluoroalkyl group having from 1 to 4 carbon atoms; L represents a divalent linking group having from 1 to 6 carbon atoms and optionally substituted with a halogen atom. m, n, p and q each indicate an integer of from 0 to 5, satisfying $1 \leq m+n \leq 5$ and $1 \leq p+q \leq 5$.)

In the general formula (III-1), $R^{23}$ and $R^{24}$ each represent a fluoroalkyl group having from 1 to 4 carbon atoms, in which at least one hydrogen atom is substituted with a fluorine atom. As specific examples of the group, there is mentioned a fluoroalkyl group, such as a fluoromethyl group, a difluoromethyl group, a trifluoromethyl group, a 2,2,2-trifluoroethyl group, a perfluoroethyl group, a perfluoropropyl group, a perfluorobutyl group, etc. Of those, preferably, $R^{23}$ and $R^{24}$ each independently represent a fluoroalkyl group having 1 or 2 carbon atoms, more preferably a difluoromethyl group, a trifluoromethyl group, a 2,2,2-trifluoroethyl group or a perfluoroethyl group.

L, m, n, p and q have the same meanings as those in the general formula (III) mentioned above.

Specific examples and preferred examples of the alkanedisulfonate compound represented by the general formula (III-1) are the same as those of the compound of the general formula (III).

The compound represented by the general formula (III-1) of the present invention can be produced according to (B) a method of transesterifying an alkanedisulfonyl dihalide compound with the corresponding phenol compound in the presence or absence of a solvent and in the presence or absence of a base; however, the production method is not limited to the method (B).

In the method (B), the amount of the phenol compound to be used is preferably from 1.6 to 30 mols relative to 1 mol of the alkanedisulfonyl dihalide compound, more preferably from 1.8 to 20 mols, even more preferably from 2 to 10 mols.

The alkanedisulfonyl dihalide compound to be used includes methanedisulfonyl dichloride, methanedisulfonyl dibromide, ethane-1,2-disulfonyl dichloride, ethane-1,2-disulfonyl dibromide, propane-1,3-disulfonyl dichloride, propane-1,3-disulfonyl dibromide, butane-1,4-disulfonyl dichloride, butane-1,4-disulfonyl dibromide, etc.

The phenol compound to be used includes 2-fluorophenol, 3-fluorophenol, 4-fluorophenol, 2,4-difluorophenol, 2,5-difluorophenol, 2,6-difluorophenol, 3,4-difluorophenol, 3,5-difluorophenol, 2,3,4-trifluorophenol, 2,3,5-trifluorophenol, 2,3,6-trifluorophenol, 2,4,5-trifluorophenol, 2,4,6-trifluorophenol, 3,4,5-trifluorophenol, 2,3,5,6-tetrafluorophenol, pentafluorophenol, 2-trifluoromethylphenol, 3-trifluoromethylphenol, 4-trifluoromethylphenol, 2-(2,2,2-trifluoroethyl)phenol, 2-(perfluoroethyl)phenol, 2,3-bis(trifluoromethyl)phenol, 2,4-bis(trifluoromethyl)phenol, 2,5-bis(trifluoromethyl)phenol, 2,6-bis(trifluoromethyl)phenol, 3,5-bis(trifluoromethyl)phenol, etc.

In the method (B), the reaction may go on with no solvent, but a solvent inert to the reaction may be used. The solvent to be used includes aliphatic hydrocarbons such as heptane, cyclohexane, etc.; halogenohydrocarbons such as dichloromethane, dichloroethane, etc.; aromatic hydrocarbons such as toluene, xylene, etc.; halogenoaromatic hydrocarbons such as chlorobenzene, fluorobenzene, etc.; ethers such as diisopropyl ether, dioxane, dimethoxyethane, etc.; esters such as ethyl acetate, butyl acetate, dimethyl carbonate, diethyl carbonate, etc.; nitriles such as acetonitrile, propionitrile, etc.; sulfoxides such as dimethyl sulfoxide, sulfolane, etc.; amides such as N,N-dimethylformamide, N,N-dimethylacetamide, etc.; and their mixtures. Of those, preferred are aliphatic or aromatic hydrocarbons and esters, such as heptane, cyclohexane, toluene, ethyl acetate, dimethyl carbonate, etc.

The amount of the solvent to be used is preferably from 0 to 30 parts by mass relative to 1 part by mass of the alkanedisulfonyl dihalide compound, more preferably from 1 to 10 parts by mass.

In the method (B), the reaction may go on with no base, but the presence of a base therein is preferred as promoting the reaction. As the base, any of an inorganic base or an organic base may be used.

The inorganic base includes potassium carbonate, sodium carbonate, calcium hydroxide and calcium oxide. The organic base includes a linear or branched aliphatic tertiary amine, a substituted or unsubstituted imidazole, pyridine or pyrimidine. Of those, preferred are trialkylamines such as trimethylamine, triethylamine, tripropylamine, tributylamine, diisopropylethylamine, etc.; pyridines such as pyridine, N,N-dimethylaminopyridine, etc.

The amount of the base to be used is preferably from 1.6 to 10 mols relative to 1 mol of the alkanedisulfonyl dihalide compound, more preferably from 2 to 6 mols, even more preferably from 2 to 3 mols.

In the method (B), the lower limit of the reaction temperature is preferably not lower than −20° C., more preferably not lower than −10° C., from the viewpoint of not lowering the reactivity. From the viewpoint of preventing any side reaction and decomposition of products, the upper limit of the reaction temperature is preferably not higher than 100° C., more preferably not higher than 80° C.

The reaction time may be suitably changed depending on the reaction temperature and the scale; however, when the reaction time is too short, then unreacted matters may remain, but on the contrary, when the reaction time is too long, then there may occur a risk of decomposition of reaction products and side reaction. Therefore, preferably, the reaction time is from 0.1 to 12 hours, more preferably from 0.2 to 6 hours.

EXAMPLES

Synthesis Examples of the compounds for use in the present invention are shown below; however, the present invention is not limited to these Synthesis Examples.

In addition, Examples of nonaqueous electrolytic solutions using any of the compounds of the present invention are shown, but the present invention is not also limited to these Examples.

Synthesis Example I-1

Synthesis of cyclohexyl-1,5,2,4-dioxadithiepine-2,2,4,4-tetraoxide (Synthetic Compound 1)

2.10 g (18.1 mmol) of trans-1,2-cyclohexanediol and 5.00 g (23.5 mmol) of methanedisulfonyl chloride were dissolved in 140 mL of ethyl acetate, and cooled to 15° C. 4.93 g (48.7 mmol) of triethylamine was added dropwise to the solution at 13 to 17° C., taking 10 minutes, and then stirred at room temperature for 3 hours. The formed salt was filtered, the solvent was concentrated under reduced pressure, and the resulting residue was purified through silica gel column chromatography (elution with ethyl acetate/hexane=1/5) to give 3.40 g (yield 73%) of a white solid, cyclohexyl-1,5,2,4-dioxadithiepine-2,2,4,4-tetraoxide.

$^1$H-NMR and the melting point of the obtained cyclohexyl-1,5,2,4-dioxadithiepine-2,2,4,4-tetraoxide were measured. The results are shown below.

$^1$H-NMR (300 MHz, CDCl$_3$): δ=5.01 (s, 2H), 4.95-4.86 (m, 2H), 2.31-2.24 (m, 2H), 1.92-1.86 (s, 2H), 1.74-1.63 (m, 2H), 1.39-1.31 (m, 2H)

m.p. 52-54° C.

Examples I-1 to I-14, Comparative Example I-1 and Comparative Example I-2

[Production of Lithium Ion Secondary Battery]

94% by mass of LiCoO$_2$ and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied onto one surface of an aluminium foil (collector), then dried, processed under pressure and blanked into a predetermined size, thereby producing a positive electrode sheet. The density of the part of the positive electrode except the collector was 3.6 g/cm³. On the other hand, 95% by mass of artificial graphite (d₀₀₂=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm³. The electrode sheet was analyzed through X-ray diffractiometry, and the ratio of the peak intensity I (110) of the (110) plane of the graphite crystal to the peak intensity I (004) of the (004) plane thereof [I (110)/I (004)] was 0.1. The positive electrode sheet, a porous polyethylene film separator and the negative electrode sheet were laminated in that order, and the nonaqueous electrolytic solution having the composition shown in Table 1 and Table 2 was added thereto to construct a 2032 coin-type battery.

[Evaluation of Low-Temperature Cycle Properties]

In a thermostatic chamber kept at 60° C., the battery produced according to the above-mentioned method was charged up to 4.2 V (final charging voltage) with a constant current of 1 C, then charged at the constant voltage of 4.2 V for 2.5 hours, and then discharged down to 3.0 V (final discharging voltage) under the constant current of 1 C. Next, in a thermostatic chamber at 0° C., this was charged up to 4.2 V with a constant current of 1 C, then charged at the constant voltage of 4.2 V for 2.5 hours, and then discharged down to a discharge voltage of 3.0 under the constant current of 1 C. The cycle was repeated up to 50 cycles. According to the equation mentioned below, the discharge capacity retention rate after 50 cycles at 0° C. was calculated. The results are shown in Tables 1 and 2.

Discharge Capacity Retention Rate (%) after 50 cycles at 0° C.=(discharge capacity after 50 cycles at 0° C./discharge capacity after 1 cycle at 0° C.)×100.

[Evaluation of Low-Temperature Property after High-temperature Charging Storage]

(i) Initial Discharge Capacity

In a thermostatic chamber at 25° C., the coin-type battery produced according to the above-mentioned method was charged up to a final voltage of 4.2 V with a constant current of 1 C and under a constant voltage for 3 hours, then the temperature of the thermostatic chamber was lowered down to 0° C., and the battery therein was discharged down to a final voltage of 2.75 V with a constant current of 1 C, thereby determining the initial discharge capacity of the battery at 0° C.

(ii) High-Temperature Charging Storage Test

Next, in a thermostatic chamber at 85° C., the coin-type battery was charged up to a final voltage of 4.2 V with a constant current of 1 C and under a constant voltage for 3 hours, and then stored while kept at 4.2 V for 3 days. Subsequently, this was put into a thermostatic chamber at 25° C., and once discharged down to a final voltage of 2.75 V with a constant current of 1 C.

(iii) Discharge Capacity after High-temperature Charging Storage

Further after this and in the same manner as in the measurement of the initial discharge capacity, the discharge capacity at 0° C. of the battery after the high-temperature charging storage (that is, after fully charged and then stored at the high temperature of 85° C. according to item (ii)) was measured.

(iv) Low-Temperature Property after High-temperature Charging Storage

The low-temperature characteristic after high-temperature charging storage of the battery was determined from the discharge capacity retention rate at 0° C. mentioned below.

Discharge Capacity Retention Rate (%) at 0° C. after high-temperature charging storage=(discharge capacity at 0° C. after high-temperature charging storage/initial discharge capacity at 0° C.)×100

The battery characteristics are shown in Tables 1 and 2.

TABLE 1

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Example I-1 | 1.2M LiPF6 EC/DMC/MEC (30/40/30) | 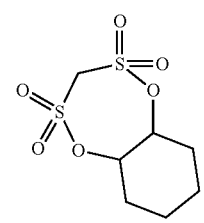 [SMILES: O=S1(=O)CS(=O)(=O)OC2CCCCC2O1] | 1 | 74 | 76 |
| Example I-2 | 1.2M LiPF6 + 0.05M LiBF4 EC/VC/DMC/MEC (29/1/40/30) | 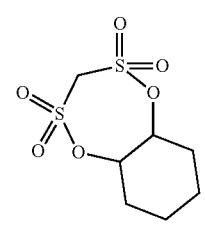 [SMILES: O=S1(=O)CS(=O)(=O)OC2CCCCC2O1] | 0.1 | 72 | 72 |

TABLE 1-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Example I-3 | 1.2M LiPF6 + 0.05M LiBF4 EC/VC/DMC/MEC (29/1/40/30) | | 1 | 85 | 86 |
| Example I-4 | 1.2M LiPF6 + 0.05M LiBF4 EC/VC/DMC/MEC (29/1/40/30) | | 3 | 81 | 83 |
| Example I-5 | 1.2M LiPF6 + 0.05M LiBF4 EC/VC/DMC/MEC (29/1/40/30) | | 7 | 78 | 79 |
| Example I-6 | 1.2M LiPF6 + 0.05M LiBF4 EC/FEC/VC/DMC/MEC (24/5/1/40/30) | | 1 | 87 | 88 |
| Example I-9 | 1.2M LiPF6 + 0.05M LiBF4 EC/VC/DMC/MEC (29/1/40/30) | | 1 | 83 | 83 |
| Example I-10 | 1.2M LiPF6 + 0.05M LiBF4 EC/VC/DMC/MEC (29/1/40/30) | | 1 | 87 | 88 |

TABLE 1-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Example I-11 | 1.2M LiPF6 + 0.05M LiBF4 EC/VC/DMC/MEC (29/1/40/30) | 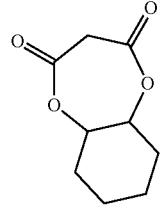 [SMILES: O=C1CC(=O)OC2CCCCC2O1] | 1 | 80 | 81 |
| Comparative Example I-1 | 1.2M LiPF6 + 0.05M LiBF4 EC/VC/DMC/MEC (29/1/40/30) | none | — | 62 | 65 |
| Comparative Example I-2 | 1.2M LiPF6 + 0.05M LiBF4 EC/VC/DMC/MEC (29/1/40/30) | 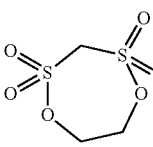 | 1 | 63 | 67 |

TABLE 2

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Example I-12 | 1.2M LiPF6 + 0.05M LiBF4 EC/VC/DMC/MEC (29/1/40/30) | 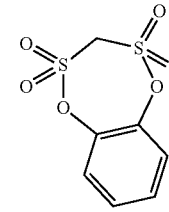 | 1 | 76 | 77 |
| Example I-13 | 1.2M LiPF6 + 0.05M LiBF4 EC/VC/DMC/MEC (29/1/40/30) | 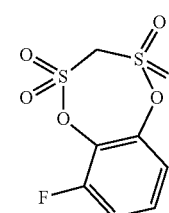 | 1 | 78 | 79 |
| Example I-14 | 1.2M LiPF6 + 0.05M LiBF4 EC/VC/DMC/MEC (29/1/40/30) | 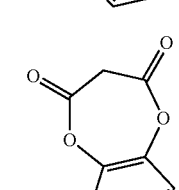 | 1 | 74 | 75 |
| Comparative Example I-1 | 1.2M LiPF6 + 0.05M LiBF4 EC/VC/DMC/MEC (29/1/40/30) | none | 1 | 62 | 65 |

TABLE 2-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Comparative Example I-2 | 1.2M LiPF6 + 0.05M LiBF4 EC/VC/DMC/MEC (29/1/40/30) | | 1 | 63 | 67 |

Examples I-15 to I-17, and Comparative Example I-5

A negative electrode sheet was produced, using silicon (elementary substance) (negative electrode active material) in place of the negative electrode active material used in Example I-3, Example I-11, Example I-12 and Comparative Example I-2. Precisely, 80% by mass of silicon (elementary substance) and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin-type batteries were produced and evaluated in the same manner as in Example I-3, Example I-11, Example I-12 and Comparative Example I-2, except that the negative electrode sheet produced herein was used. The results are shown in Table 3.

TABLE 3

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
|---|---|---|---|---|---|
| Example I-15 | 1.1M LiPF6 + 0.05M LiBF4 EC/VC/DMC/MEC (29/1/40/30) | | 1 | 74 | 75 |
| Example I-16 | 1.1M LiPF6 + 0.05M LiBF4 EC/VC/DMC/MEC (29/1/40/30) | | 1 | 71 | 72 |
| Example I-17 | 1.1M LiPF6 + 0.05M LiBF4 EC/VC/DMC/MEC (29/1/40/30) | | 1 | 71 | 72 |
| Comparative Example I-5 | 1.1M LiPF6 + 0.05M LiBF4 EC/VC/DMC/MEC (29/1/40/30) | | 1 | 55 | 57 |

Examples I-18 to I-20, and Comparative Example I-6

A positive electrode sheet was produced by changing the positive electrode active material used in Example I-3, Example I-15, Comparative Example I-1 and Comparative Example I-2 to $LiFePO_4$ (positive electrode active material) coated with amorphous carbon. Concretely, 90% by mass of $LiFePO_4$ coated with amorphous carbon and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet. Coin-type batteries were produced and evaluated in the same manner as in Example I-3, Example I-11, Example I-12 and Comparative Example I-2, except that the positive electrode sheet thus produced herein was used and the final charging voltage was changed to 3.6 V and the final discharging voltage was changed to 2.0 V in battery evaluation. The results are shown in Table 4.

The lithium secondary batteries of Examples I-1 to I-14 were all remarkably bettered in point of the electrochemical characteristics in a broad temperature range thereof, as compared with the lithium secondary battery of Comparative Example I-1 in which the specific compound was not added to the nonaqueous electrolytic solution of the first aspect of the present invention, and that of Comparative Example I-2 in which 1,5,2,4-dioxadithiepane 2,2,4,4-tetraoxide described in PTL 1 was added to the nonaqueous electrolytic solution. From the above, it has been clarified that the advantageous effect of the present invention, especially that of the first aspect of the present invention is peculiar to the nonaqueous electrolytic solution of an electrolyte salt dissolved in a nonaqueous solvent that contains the compound represented by the general formula (II) in an amount of from 0.001 to 10% by mass.

In addition, from comparison of Examples I-15 to I-17 with Comparative Example I-5, and from comparison of Examples I-18 to I-20 with Comparative Example I-6, the same advantageous effect is observed in the case where silicon (elementary substance) Si was used as the negative electrode and in the case where a lithium-containing olivine-type iron phosphate ($LiFePO_4$) was used as the positive electrode. Accord-

TABLE 4

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) after 50 cycles at 0° C. | Discharge Capacity Retention Rate (%) at 0° C. after 85° C. high-temperature charging storage |
| --- | --- | --- | --- | --- | --- |
| Example I-18 | 1.1M LiPF6 + 0.05M LiBF4 EC/VC/DMC/MEC (29/1/40/30) | | 1 | 76 | 78 |
| Example I-19 | 1.1M LiPF6 + 0.05M LiBF4 EC/VC/DMC/MEC (29/1/40/30) | | 1 | 73 | 75 |
| Example I-20 | 1.1M LiPF6 + 0.05M LiBF4 EC/VC/DMC/MEC (29/1/40/30) | | 1 | 71 | 74 |
| Comparative Example I-6 | 1.1M LiPF6 + 0.05M LiBF4 EC/VC/DMC/MEC (29/1/40/30) | | 1 | 58 | 60 | ingly, it is obvious that the advantageous effect of the present invention does not depend on any specific positive electrode or negative electrode.

Further, the nonaqueous electrolytic solution of the present invention, especially that of the first aspect of the present invention has an effect of improving the discharge properties of lithium primary batteries in a broad temperature range.

Synthesis Example II-1

Synthesis of bis(2,4-difluorophenyl)methanedisulfonate (Synthetic Compound 2)

2.97 g (22.8 mmol) of 2,4-difluorophenol was dissolved in 25 mL of ethyl acetate, and 2.31 g (22.8 mmol) of triethylamine was added thereto and cooled to 5° C. 2.43 g (11.4 mmol) of methanedisulfonyl chloride was added dropwise to the solution at 10° C. or lower, and stirred at room temperature for 1 hour. The reaction liquid was washed with 10 mL of water, the organic layer was concentrated under reduced pressure, and the resulting residue was purified through silica gel column chromatography (elution with hexane/ethyl acetate=5/1) to give 2.23 g (yield 49%) of the intended bis(2,4-difluorophenyl)methanedisulfonate.

$^1$H-NMR of the obtained bis(2,4-difluorophenyl)methanedisulfonate was measured to identify the structure thereof. The results are shown below.

$^1$H-NMR (300 MHz, CDCl$_3$): δ=7.47-7.39 (m, 2H), 7.05-6.91 (m, 4H), 5.12 (s, 2H)

Synthesis Example II-2

Synthesis of bis(pentafluorophenyl)methanedisulfonate (Synthetic Compound 3)

2.00 g (9.4 mmol) of methanedisulfonyl dichloride and 3.81 g (20.7 mmol) of pentafluorophenol were dissolved in 25 mL of ethyl acetate, and cooled to 5° C. 2.28 g (22.5 mmol of triethylamine was added dropwise to the solution at 10° C. or lower, and stirred at room temperature for 3 hours. The formed salt was filtered, the solvent was concentrated under reduced pressure, and the resulting residue was purified through silica gel column chromatography (elution with hexane/ethyl acetate=2/1) to give 0.83 g (yield 18%) of the intended bis(pentafluorophenyl)methanedisulfonate.

$^1$H-NMR of the obtained bis(pentafluorophenyl)methanedisulfonate was measured to identify the structure thereof. The results are shown below.

$^1$H-NMR (300 MHz, CDCl$_3$): δ=5.31 (s, 2H)

Examples II-1 to II-22, Comparative Examples II-1 to II-4

Production of Lithium Ion Secondary Battery

94% by mass of LiCoO$_2$ and 3% by mass of acetylene black (electroconductive agent) were mixed, and added to and mixed in a solution previously prepared by dissolving 3% by mass of polyvinylidene fluoride (binder) in 1-methyl-2-pyrrolidone, thereby preparing a positive electrode mixture paste. The positive electrode mixture paste was applied onto one surface of an aluminium foil (collector), then dried, processed under pressure and blanked into a predetermined size, thereby producing a positive electrode sheet. The density of the part of the positive electrode except the collector was 3.6 g/cm$^3$. On the other hand, 95% by mass of artificial graphite (d$_{002}$=0.335 nm, negative electrode active material) was added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto one surface of a copper foil (collector), dried, processed under pressure and blanked into a predetermined size, thereby producing a negative electrode sheet. The density of the part of the negative electrode except the collector was 1.5 g/cm$^3$. The electrode sheet was analyzed through X-ray diffractiometry, and the ratio of the peak intensity (110) of the (110) plane of the graphite crystal to the peak intensity I (004) of the (004) plane thereof [I (110)/I (004)] was 0.1. The positive electrode sheet, a porous polyethylene film separator and the negative electrode sheet were laminated in that order, and the nonaqueous electrolytic solution having the composition shown in Tables 5 and 6 was added thereto to construct a 2032 coin-type battery.

In the same manner as that of the method of [Evaluation of Low-Temperature Property after high-temperature charging storage], the batteries were tested for (i) initial discharge capacity, (ii) high-temperature charging storage test, (iii) discharge capacity after high-temperature charging storage and (iv) low-temperature property after high-temperature charging storage.

The condition in producing the batteries and the battery characteristics are shown in Table 5 and 6.

TABLE 5

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-1 | 1.1M LiPF6 EC/DMC/MEC (30/40/30) |  | 1 | 74 |
| Example II-2 | 1.1M LiPF6 + 0.05M LiBF4 EC/VC/DMC/MEC (29/1/40/30) | 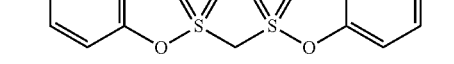 | 0.1 | 71 |

TABLE 5-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-3 | 1.1M LiPF6 + 0.05M LiBF4 EC/VC/DMC/MEC (29/1/40/30) | | 1 | 85 |
| Example II-4 | 1.1M LiPF6 + 0.05M LiBF4 EC/VC/DMC/MEC (29/1/40/30) | | 3 | 81 |
| Example II-5 | 1.1M LiPF6 + 0.05M LiBF4 EC/VC/DMC/MEC (29/1/40/30) | | 7 | 78 |
| Example II-6 | 1.1M LiPF6 + 0.05M LiBF4 EC/FEC/VC/DMC/MEC (24/5/1/40/30) | | 1 | 88 |
| Example II-7 | 1.1M LiPF6 + 0.05M LiBF4 EC/VC/DMC/MEC (29/1/40/30) | | 1 | 78 |
| Example II-8 | 1.1M LiPF6 + 0.05M LiBF4 EC/VC/DMC/MEC (29/1/40/30) | | 1 | 77 |
| Example II-9 | 1.1M LiPF6 + 0.05M LiBF4 EC/VC/DMC/MEC (29/1/40/30) | | 1 | 74 |
| Example II-10 | 1.1M LiPF6 + 0.05M LiBF4 EC/VC/DMC/MEC (29/1/40/30) | | 1 | 83 |
| Example II-11 | 1.1M LiPF6 + 0.05M LiBF4 EC/VC/DMC/MEC (29/1/40/30) | | 1 | 80 |
| Example II-12 | 1.1M LiPF6 + 0.05M LiBF4 EC/VC/DMC/MEC (29/1/40/30) | | — | 81 |

TABLE 5-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-13 | 1.1M LiPF6 + 0.05M LiBF4 EC/VC/DMC/MEC (29/1/40/30) | bis(2,4-difluorophenyl) ethane-1,2-disulfonate | 1 | 80 |
| Example II-14 | 1.1M LiPF6 + 0.05M LiBF4 EC/VC/DMC/MEC (29/1/40/30) | bis(2,4-difluorophenyl) propane-1,3-disulfonate | 1 | 78 |
| Example II-15 | 1.1M LiPF6 + 0.05M LiBF4 EC/VC/DMC/MEC (29/1/40/30) | bis(2,4-dichlorophenyl) methanedisulfonate | 1 | 79 |
| Comparative Example II-1 | 1.1M LiPF6 + 0.05M LiBF4 EC/VC/DMC/MEC (29/1/40/30) | none | — | 62 |
| Comparative Example II-2 | 1.1M LiPF6 + 0.05M LiBF4 EC/VC/DMC/MEC (29/1/40/30) | diphenyl methanedisulfonate | 1 | 64 |

TABLE 6

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-16 | 1.1M LiPF6 + 0.05M LiBF4 EC/VC/DMC/MEC (29/1/40/30) | bis(2-fluorophenyl) malonate | 1 | 76 |
| Example II-17 | 1.1M LiPF6 + 0.05M LiBF4 EC/VC/DMC/MEC (29/1/40/30) | bis(4-fluorophenyl) malonate | 1 | 75 |
| Example II-18 | 1.1M LiPF6 + 0.05M LiBF4 EC/VC/DMC/MEC (29/1/40/30) | bis(3-fluorophenyl) malonate | 1 | 74 |
| Example II-19 | 1.1M LiPF6 + 0.05M LiBF4 EC/VC/DMC/MEC (29/1/40/30) | bis(2,4-difluorophenyl) malonate | 1 | 83 |

TABLE 6-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-20 | 1.1M LiPF6 + 0.05M LiBF4 EC/VC/DMC/MEC (29/1/40/30) | 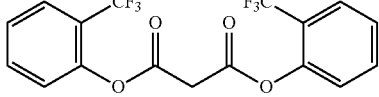 | 1 | 81 |
| Example II-21 | 1.1M LiPF6 + 0.05M LiBF4 EC/VC/DMC/MEC (29/1/40/30) | 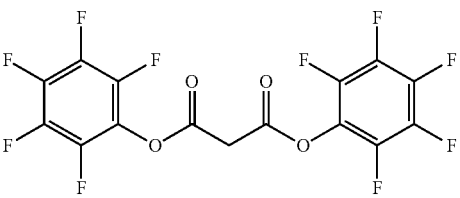 [SMILES: O=C(CC(=O)Oc1c(F)c(F)c(F)c(F)c1F)Oc1c(F)c(F)c(F)c(F)c1F] | 1 | 78 |
| Example II-22 | 1.1M LiPF6 + 0.05M LiBF4 EC/VC/DMC/MEC (29/1/40/30) | 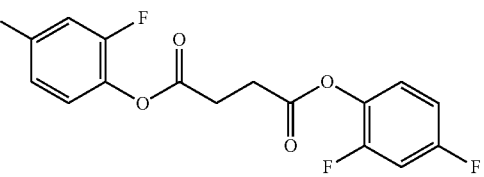 | 1 | 81 |
| Comparative Example II-1 | 1.1M LiPF6 + 0.05M LiBF4 EC/VC/DMC/MEC (29/1/40/30) | none | — | 62 |
| Comparative Example II-3 | 1.1M LiPF6 + 0.05M LiBF4 EC/VC/DMC/MEC (29/1/40/30) | 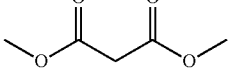 | 1 | 63 |
| Comparative Example II-4 | 1.1M LiPF6 + 0.05M LiBF4 EC/VC/DMC/MEC (29/1/40/30) | 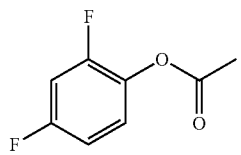 | 1 | 64 |

Example II-23 and Example II-24, Comparative Example II-5 and Comparative Example II-6

A negative electrode sheet was produced, using silicon (elementary substance) (negative electrode active material) in place of the negative electrode active material used in Example II-3, Example II-16, Comparative Example II-2 and Comparative Example II-3. Precisely, 80% by mass of silicon (elementary substance) and 15% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a negative electrode mixture paste. The negative electrode mixture paste was applied onto a copper foil (collector), dried, processed under pressure, and blanked into a predetermined size, thereby producing a negative electrode sheet. Coin-type batteries were produced and evaluated in the same manner as in Example II-3, Example II-16, Comparative Example II-2 and Comparative Example II-3, except that the negative electrode sheet produced herein was used. The results are shown in Table 7.

TABLE 7

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-23 | 1.1M LiPF6 + 0.05M LiBF4 EC/VC/DMC/MEC (29/1/40/30) | 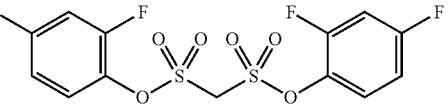 | 1 | 72 |

TABLE 7-continued

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-24 | 1.1M LiPF6 + 0.05M LiBF4 EC/VC/DMC/MEC (29/1/40/30) | bis(difluorophenyl) malonate structure | 1 | 68 |
| Comparative Example II-5 | 1.1M LiPF6 + 0.05M LiBF4 EC/VC/DMC/MEC (29/1/40/30) | diphenylmethane disulfonate structure | 1 | 57 |
| Comparative Example II-6 | 1.1M LiPF6 + 0.05M LiBF4 EC/VC/DMC/MEC (29/1/40/30) | dimethyl malonate structure | 1 | 55 |

Example 11-25 and Example II-26, Comparative Example II-7 and Comparative Example II-8

A positive electrode sheet was produced by changing the positive electrode active material used in Example II-3, Example II-16, Comparative Example II-2 and Comparative Example II-3 to LiFePO$_4$ (positive electrode active material) coated with amorphous carbon. Concretely, 90% by mass of lithium-containing olivine-type iron phosphate (LiFePO$_4$) and 5% by mass of acetylene black (electroconductive agent) were mixed, and added to and mixed in a solution previously prepared by dissolving 5% by mass of polyvinylidene fluoride (binder) in 1-methyl-2-pyrrolidone, thereby preparing a positive electrode mixture paste. The positive electrode mixture paste was applied onto an aluminium foil (collector), dried, processed under pressure and blanked into a predetermined size, thereby producing a positive electrode sheet.

Coin-type batteries were produced and evaluated in the same manner as in Example II-3, Example II-16, Comparative Example II-2 and Comparative Example II-3, except that the positive electrode sheet thus produced herein was used and the final charging voltage was changed to 3.6 V and the final discharging voltage was changed to 2.0 V in battery evaluation. The results are shown in Table 8.

TABLE 8

| | Composition of Electrolyte Salt Composition of Nonaqueous Electrolytic Solution (ratio by volume of solvents) | Compound | Amount of Compound Added (content (wt %) in nonaqueous electrolytic solution) | Discharge Capacity Retention Rate (%) at 0° C. after 85° C. high-temperature charging storage |
|---|---|---|---|---|
| Example II-25 | 1.1M LiPF6 + 0.05M LiBF4 EC/VC/DMC/MEC (29/1/40/30) | bis(difluorophenyl) methanedisulfonate structure | 1 | 85 |
| Example II-26 | 1.1M LiPF6 + 0.05M LiBF4 EC/VC/DMC/MEC (29/1/40/30) | bis(difluorophenyl) malonate structure | 1 | 82 |
| Comparative Example II-7 | 1 1M LiPF6 + 0.05M LiBF4 EC/VC/DMC/MEC (29/1/40/30) | diphenylmethane disulfonate structure | 1 | 60 |
| Comparative Example II-8 | 1.1M LiPF6 + 0.05M LiBF4 EC/VC/DMC/MEC (29/1/40/30) | dimethyl malonate structure | 1 | 58 |

The lithium secondary batteries of Examples II-1 to II-22 were all remarkably bettered in point of the electrochemical characteristics in a broad temperature range thereof, as compared with the lithium secondary battery of Comparative Example II-1 in which the specific compound was not added to the nonaqueous electrolytic solution of the second aspect of the present invention, and those of Comparative Example II-2, Comparative Example II-3 and Comparative Example II-4 in which diphenylmethane disulfonate described in PTL 2 or dimethyl malonate described in PTL 3 or 2,4-difluorophenyl acetate described in PTL 4 was added to the nonaqueous electrolytic solution. From the above, it has been clarified that the advantageous effect of the present invention, especially that of the second aspect of the present invention is peculiar to the nonaqueous electrolytic solution of an electrolyte salt dissolved in a nonaqueous solvent that contains the compound represented by the general formula (III) in an amount of from 0.001 to 10% by mass.

In a thermostatic chamber kept at 60° C., the lithium secondary battery produced under the same condition as in Examples II-3, II-10 and II-11 and Comparative Example II-1 was charged up to a final voltage of 4.2 V for 3 hours with a constant current of 1 C and a constant voltage, and then discharged under the constant current of 1 C to a discharging voltage of 3.0 V. This is one cycle. The cycle was repeated up to 200 cycles. According to the equation mentioned below, the capacity retention rate after 200 cycles was calculated.

Capacity Retention Rate (%)=(discharge capacity after 200 cycles/discharge capacity after 1 cycle)×100.

As a result, the capacity retention rate after 200 cycles was 81% in Example II-3, 78% in Example II-10, 76% in Example II-11 and 66% in Comparative Example II-1. The data confirm that the batteries of those Examples have markedly improved high-temperature cycle properties.

In addition, from comparison of Example II-23 and Example II-24 with Comparative Example II-5 and Comparative Example II-6, and from comparison of Example II-25 and Example II-26 with Comparative Example II-7 and Comparative Example II-8, the same advantageous effect is seen in the case where silicon (elementary substance) Si was used as the negative electrode and in the case where a lithium-containing olivine-type iron phosphate (LiFePO$_4$) was used as the positive electrode. Accordingly, it is obvious that the advantageous effect of the present invention does not depend on any specific positive electrode or negative electrode.

Further, the nonaqueous electrolytic solution of the second aspect of the present invention has an effect of improving the discharge properties of lithium primary batteries in a broad temperature range.

Industrial Applicability

The present invention, especially using the nonaqueous electrolytic solution of the first aspect and second aspect of the present invention, provides energy storage devices excellent in electrochemical characteristics in a broad temperature range. In particular, when the nonaqueous electrolytic solution is used for energy storage devices to be mounted on hybrid electric vehicles, plug-in hybrid electric vehicles, battery electric vehicles, etc., there can be obtained energy storage devices having improved electrochemical characteristics in a broad temperature range.

The invention claimed is:

1. A nonaqueous electrolytic solution of an electrolyte salt dissolved in a nonaqueous solvent, which comprises from 0.001 to 10% by mass of a compound of formula (I):

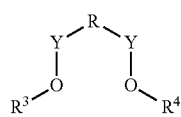

(I)

wherein

Y is a group —C(=O)— or a group —S(=O)$_2$—;

R$^3$ and R$^4$ bonding to each other are a cycloalkanediyl group having from 5 to 12 carbon atoms or a benzenediyl group, and the cycloalkanediyl group and the benzenediyl group optionally have a substituent;

R is —C(R$^1$)(R$^2$)— or -L-;

R$^1$ and R$^2$ are each independently a hydrogen atom, a halogen atom, or an alkyl group having from 1 to 4 carbon atoms; and L is a divalent linking group having from 1 to 6 carbon atoms and optionally substituted with a halogen atom.

2. The nonaqueous electrolytic solution according to claim 1, wherein
R is —C(R$^1$)(R$^2$).

3. The nonaqueous electrolytic solution according to claim 1, wherein the nonaqueous solvent comprises a cyclic carbonate and a linear ester.

4. The nonaqueous electrolytic solution according to claim 3, wherein the cyclic carbonate is at least one selected from the group consisting of ethylene carbonate, propylene carbonate, 1,2-butylene carbonate, 2,3-butylene carbonate, 4-fluoro-1,3-dioxolan-2-one, trans or cis-4,5-difluoro-1,3-dioxolan-2-one, vinylene carbonate, and vinylethylene carbonate.

5. The nonaqueous electrolytic solution according to claim 3, wherein the linear ester is an asymmetric linear carbonate selected from the group consisting of methyl ethyl carbonate, methyl propyl carbonate, methyl isopropyl carbonate, methyl butyl carbonate and ethyl propyl carbonate, a symmetric linear carbonate selected from the group consisting of dimethyl carbonate, diethyl carbonate, dipropyl carbonate and dibutyl carbonate, a linear carboxylate, or any combination thereof.

6. The nonaqueous electrolytic solution according to claim 5, wherein the linear ester is a methyl group-comprising linear ester selected from the group consisting of methyl ethyl carbonate, methyl propyl carbonate, methyl isopropyl carbonate, methyl butyl carbonate, dimethyl carbonate, methyl propionate, methyl acetate and ethyl acetate.

7. The nonaqueous electrolytic solution according to claim 1, wherein the electrolyte salt comprises at least one selected from the group consisting of LiPF$_6$, LiPO$_2$F$_2$, Li$_2$PO$_3$F, LiBF$_4$, LiN(SO$_2$CF$_3$)$_2$, LiN(SO$_2$C$_2$F$_5$)$_2$, LiN(SO$_2$F)$_2$, lithium difluorobis[oxalate-O,O']phosphate and lithium tetrafluoro[oxalate-O,O']phosphate.

8. The nonaqueous electrolytic solution according to claim 1, wherein a concentration of the electrolyte salt is from 0.3 to 2.5 M relative to the nonaqueous solvent therein.

9. An energy storage device comprising a positive electrode, a negative electrode, and a nonaqueous electrolytic solution of an electrolyte salt dissolved in a nonaqueous solvent, wherein the nonaqueous electrolytic solution is the nonaqueous electrolytic solution of claim 1.

10. The energy storage device according to claim 9, wherein the positive electrode active material is a composite metal oxide with lithium that comprises at least one selected from the group consisting of cobalt, manganese and nickel, or a lithium-comprising olivine-type phosphate that comprises at least one selected from the group consisting of iron, cobalt, nickel and manganese.

11. The energy storage device according to claim 9, wherein the negative electrode active material comprises at least one selected from the group consisting of lithium metal, lithium alloy, and carbon material capable of absorbing and releasing lithium, tin, tin compounds, silicon, silicon compounds, and lithium titanate compounds.

* * * * *